(12) United States Patent
Currie et al.

(10) Patent No.: US 10,219,893 B2
(45) Date of Patent: Mar. 5, 2019

(54) INTRAOCULAR LENS (IOL)

(71) Applicant: Tekia, Inc., Irvine, CA (US)

(72) Inventors: Gene Currie, Irvine, CA (US); Larry W. Blake, Irvine, CA (US)

(73) Assignee: TEKIA, INC., Irvine, CA (US)

( * ) Notice: Subject to any disclaimer, the term of this patent is extended or adjusted under 35 U.S.C. 154(b) by 0 days.

(21) Appl. No.: 15/330,088

(22) Filed: Aug. 4, 2016

(65) Prior Publication Data
US 2017/0042665 A1 Feb. 16, 2017

Related U.S. Application Data

(63) Continuation of application No. 13/815,725, filed on Mar. 15, 2013, now Pat. No. 9,427,313, which is a continuation-in-part of application No. 13/471,418, filed on May 14, 2012, now abandoned, which is a continuation-in-part of application No. 11/312,553, filed on Dec. 21, 2005, now Pat. No. 8,216,308, which is a continuation-in-part of application No. 11/249,358, filed on Oct. 14, 2005, now abandoned, and a continuation-in-part of application No. 10/942,992, filed on Sep. 17, 2004, now Pat. No. 7,435,258.

(51) Int. Cl.
*A61F 2/16* (2006.01)
*A61F 2/14* (2006.01)

(52) U.S. Cl.
CPC .......... *A61F 2/1624* (2013.01); *A61F 2/1627* (2013.01); *A61F 2/15* (2015.04); *A61F 2/1616* (2013.01); *A61F 2/1629* (2013.01); *A61F 2002/169* (2015.04); *A61F 2002/1681* (2013.01); *A61F 2002/1682* (2015.04); *A61F 2002/1689* (2013.01); *A61F 2002/1696* (2015.04)

(58) Field of Classification Search
CPC .... A61F 2/1616; A61F 2/1624; A61F 2/1629; A61F 2002/1689; A61F 2002/169; A61F 2002/1682
See application file for complete search history.

(56) References Cited

U.S. PATENT DOCUMENTS

| | | | |
|---|---|---|---|
| 7,008,448 B2 * | 3/2006 | Lipshitz | A61F 2/1613 623/6.31 |
| 2003/0135272 A1 * | 7/2003 | Brady | A61F 2/1629 623/6.37 |
| 2004/0220666 A1 * | 11/2004 | Cumming | A61F 2/1629 623/6.18 |
| 2011/0040376 A1 * | 2/2011 | Christie | A61F 2/1613 623/6.17 |

* cited by examiner

*Primary Examiner* — David H Willse
*Assistant Examiner* — Javier Blanco
(74) *Attorney, Agent, or Firm* — William L. Klima; Klima Law

(57) ABSTRACT

An improved intraocular lens, for example, an accommodating intraocular lens including a lens optic, the lens optic including a ring-shaped lens optic portion and/or a light window.

7 Claims, 24 Drawing Sheets

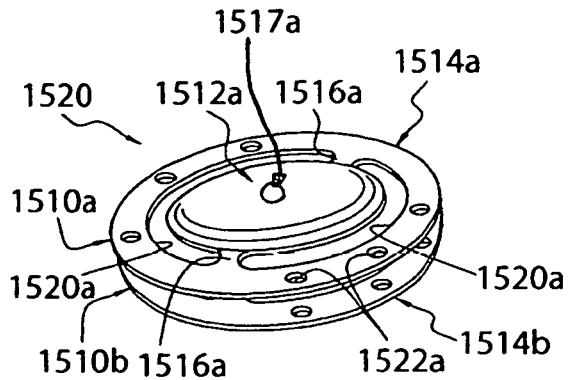
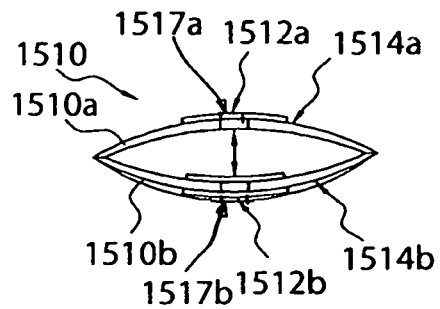
FIG. 21    FIG. 22
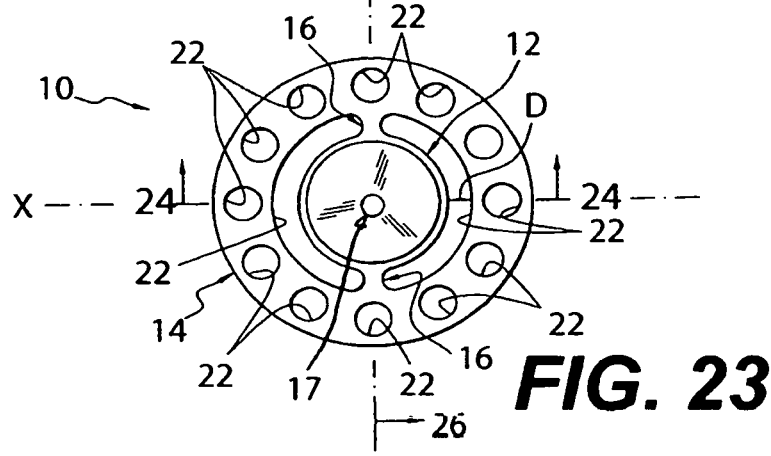
FIG. 23
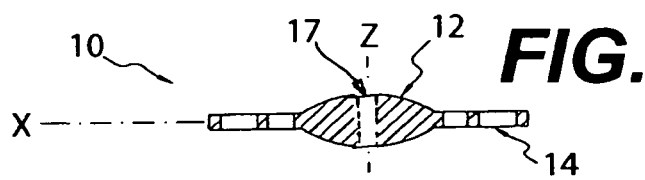
FIG. 24
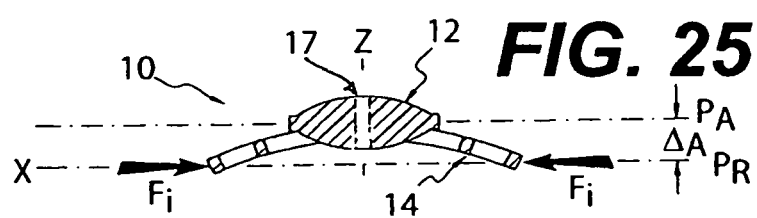
FIG. 25
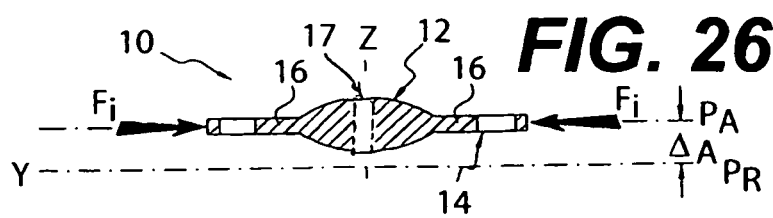
FIG. 26

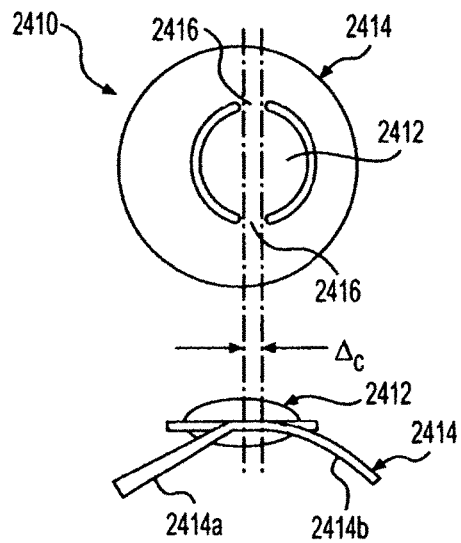
FIG. 53
FIG. 54
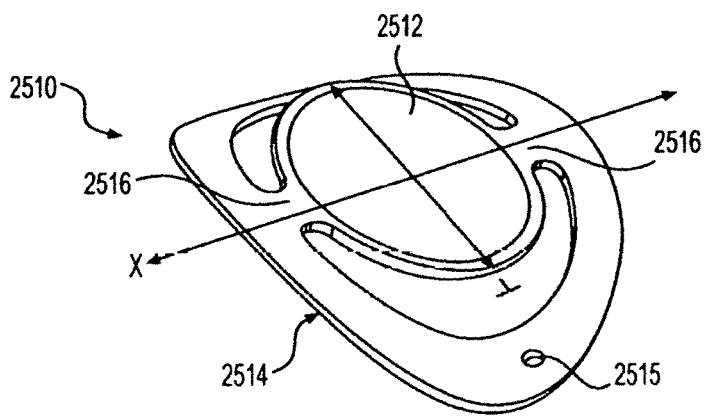
FIG. 55
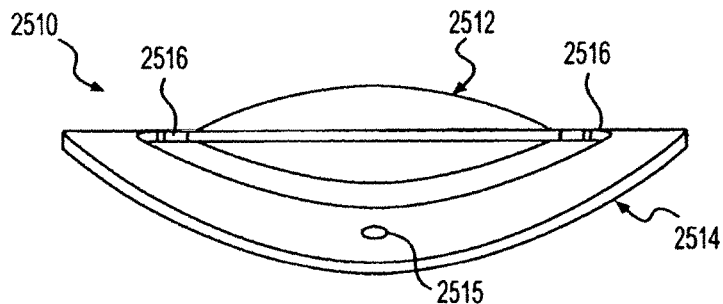
FIG. 56

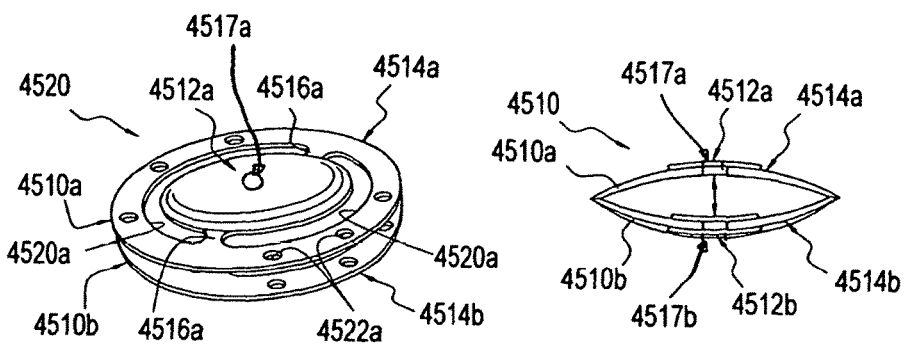
FIG. 77  FIG. 78
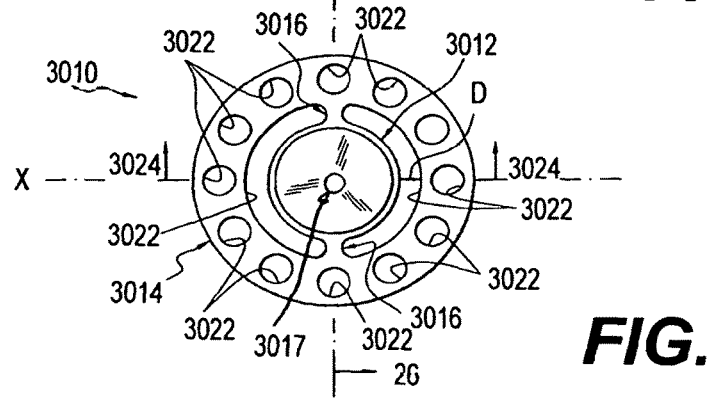
FIG. 79
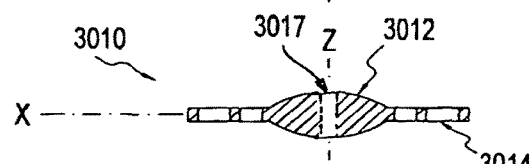
FIG. 80
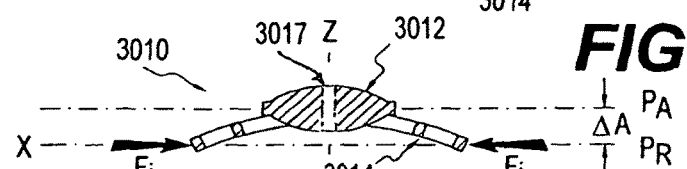
FIG. 81
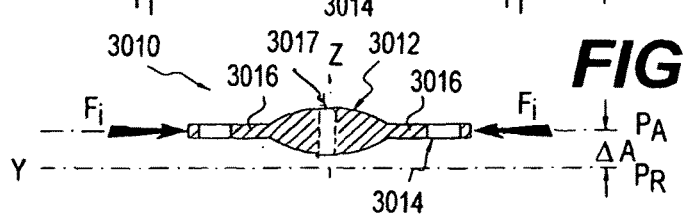
FIG. 82

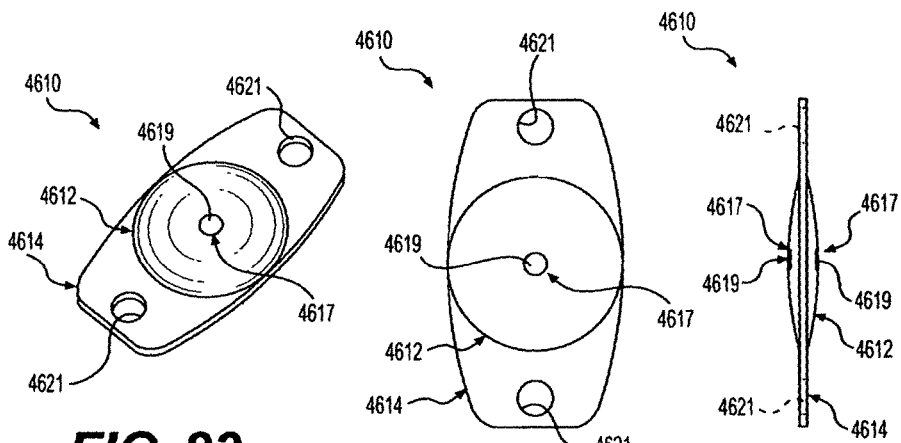
FIG. 83  FIG. 84  FIG. 85
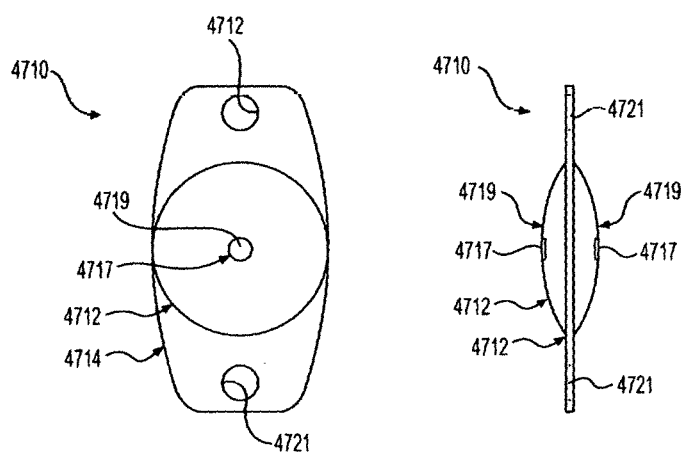
FIG. 86  FIG. 87

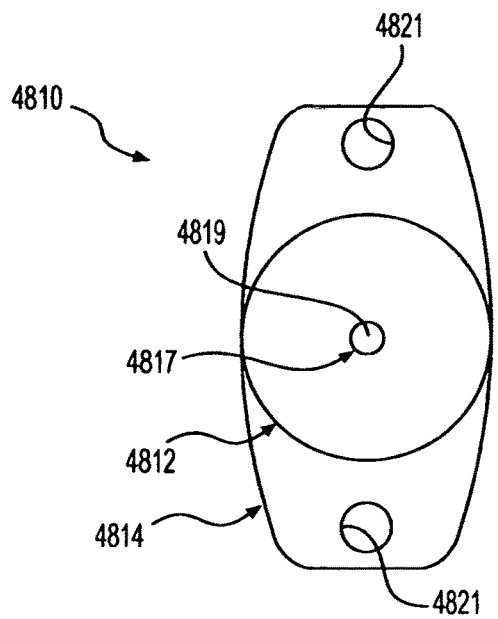 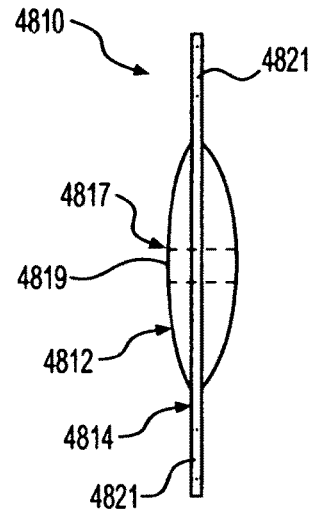
FIG. 88  FIG. 89
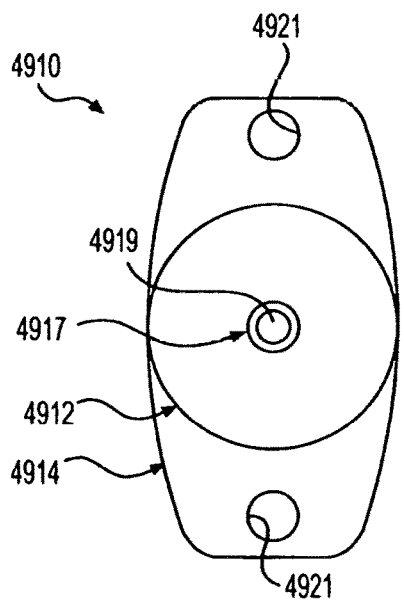 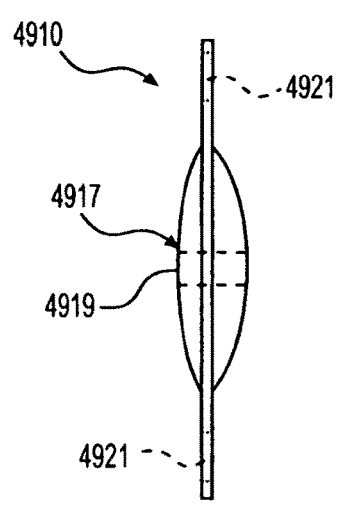
FIG. 90  FIG. 91

INTRAOCULAR LENS (IOL)

RELATED APPLICATIONS

This is a Continuation of U.S. Patent Application entitled "Intraocular Lens (IOL), application Ser. No. 13/815,725, filed on Mar. 15, 2013, now U.S. Pat. No. 9,427,313, which is a Continuation-In-Part (CIP) of U.S. Patent Application entitled "Intraocular Lens (IOL)", application Ser. No. 13/471,418, filed on May 14, 2012, now abandoned, which is a Continuation-In-Part (CIP) of U.S. Patent Application entitled "Accommodating Artificial Ocular Lens (AAOL) Device", application Ser. No. 11/312,553 filed on Dec. 21, 2005, now U.S. Pat. No. 8,216,308, which is a Continuation-In-Part (CIP) of U.S. Patent Application entitled "Refractive Corrective Lens (RCL)", application Ser. No. 11/249,358 filed on Oct. 14, 2005, now abandoned, and U.S. patent application Ser. No. 10/942,992 filed on Sep. 17, 2004, now U.S. Pat. No. 7,435,258, and all of these applications are incorporated by reference herein.

FIELD

An artificial ocular lens (AOL), in particular an accommodating artificial ocular lens (AAOL) device. A preferred embodiment of the accommodating artificial ocular lens (AAOL) device according to the present invention includes a posterior chamber accommodating artificial ocular lens (pc-AAOL) device for use in the posterior chamber of the eye outside the capsular bag or inside the capsular bag (i.e. after cataract or clear natural lens removal). Preferably, the accommodating artificial ocular lens (AAOL) according to the present invention is a deformable accommodating artificial ocular lens (AAOL) for implantation through a small incision in the eye.

Also, an intraocular lens (IOL) device, for example, an accommodating intraocular lens (AIOL) device providing accommodation of vision of the eye.

BACKGROUND OF THE INVENTION

Currently, there exists a high level of cataract lens surgeries performed in the United States and in other countries and territories throughout the world. These cataract lens surgeries involve the removal of the natural lens, typically by phacoemulsification, followed by the implantation of an aphakic intraocular lens (AIOL). Further, more recently phakic intraocular lens (PIOL), for example, the implantable contact lens (ICL) are implanted with the natural lens still intact.

Most lens surgeries are performed using an intraocular lens providing little if any accommodation of the eye. Specifically, the intraocular lens is implanted into the eye, and once healing of the eye has occurred, there is very little movement of the intraocular lens in a manner to focus the eye by accommodation like the natural crystalline lens of the eye.

There has been much interest in creating and designing intraocular lens configured to provide accommodation the same or similar to the natural crystalline lens of the eye, or provide accommodation in an alternative manner. It is believed that the next generation of intraocular lenses will be accommodating intraocular lenses that provide a significant amount of accommodation of at least one (1) diopter or more. So far, most accommodating intraocular lenses being clinically studied provide one (1) diopter or less of accommodation of the eye. Thus, there now exists a need for an accommodating intraocular lens that can provide a substantial amount of accommodation of the eye, desirably, providing one (1) or more diopters of accommodation of the eye.

The subject matter is directed to an intraocular lens (IOL), for example, an accommodating intraocular lens (AIOL) configured to provide for substantial accommodation of the eye once implanted.

Currently, there exists a high level of cataract lens surgeries performed in the United States and in other countries and territories throughout the world. These cataract lens surgeries involve the removal of the natural crystalline lens, typically by phacoemulsification, followed by the implantation of an intraocular lens (IOL).

Most cataract lens surgeries are performed using an intraocular lens providing little if any accommodation of the eye. Specifically, the intraocular lens is implanted into the capsular bag of the eye, and once healing of the eye has occurred, there is very little movement of the intraocular lens in a manner to focus the eye by accommodation like the natural crystalline lens of the eye.

There has been much interest in creating and designing intraocular lenses (IOLs) configured to provide accommodation the same or similar to the natural crystalline lens of the eye. It is believed that the next generation of intraocular lenses (IOLs) will be accommodating intraocular lenses (AIOLs) that will provide a significant amount of accommodation of at least one (1) diopter or more. So far, most accommodating intraocular lenses (AIOLs) being clinically studied provide one (1) diopter or less of accommodation of the eye. Thus, there now exists a need for an accommodating intraocular lens that can provide a substantial amount of accommodation of the eye, desirably, providing one (1) or more diopters of accommodation of the eye. Further, there now exists a need for an accommodating artificial ocular lens (AAOL) configured to be inserted into the posterior chamber of the eye outside the capsular bag with the natural lens in place or removed, or inside the capsular bag.

The present invention is directed to an accommodating artificial ocular lens (AAOL) device such as an accommodating intraocular lens (AIOL) device configured in a manner that may provide for substantial accommodation of the eye.

SUMMARY

A first object is to provide an improved accommodating artificial ocular lens (AAOL).

A second object is to provide an accommodating artificial ocular lens (AAOL) including an lens optic portion flexibly or resiliently connected to a lens plate haptic portion.

A third object is to provide an accommodating artificial ocular lens (AAOL) including an lens optic portion flexibly or resiliently connected to a lens plate haptic portion configured to bow within the eye to provide accommodation of the eye.

A fourth object is to provide an accommodating artificial ocular lens (AAOL) including a lens optic portion connected to a bowing lens plate haptic portion configured to bow within the eye and move said lens optic portion to provide accommodation of the eye.

A fifth object is to provide an accommodating artificial ocular lens (AAOL) including a lens optic portion connected to a lens plate haptic portion configured to bow relative to a length axis of the accommodating artificial ocular lens (AAOL).

A sixth object is to provide an accommodating artificial ocular lens (AAOL) including a lens optic portion connected to a lens plate haptic portion configured to bow relative to a width axis of the lens plate haptic portion.

A seventh object is to provide an accommodating artificial ocular lens (AAOL) including a lens optic portion connected to a lens plate haptic portion configured to bow relative to both the length axis and width axis of the lens plate haptic portion.

An eighth object is to provide an accommodating artificial ocular lens (AAOL) including a lens optic portion connected to a lens plate haptic portion configured to bow in three-dimensions (3D) within the eye.

A ninth object is to provide an accommodating artificial ocular lens (AAOL) including a lens optic portion connected to a lens plate haptic portion, the lens plate haptic portion being a bowing lens plate haptic portion for moving said lens optic portion within the eye to provide accommodation of the eye.

A tenth object is to provide an accommodating artificial ocular lens (AAO) including a lens optic portion connected to a lens plate haptic portion by at least by one flexible arm.

An eleventh object is to provide an accommodating artificial ocular lens (AAOL) including a lens optic portion connected to a lens plate haptic portion and configured to move the lens optic portion relative to the lens plate haptic portion when force is applied to the edge of the lens plate haptic portion.

A twelfth object is to provide an accommodating artificial ocular lens (AAOL) including a lens optic portion connected to a lens plate haptic portion, the lens optic portion being separate and spaced apart from the lens plate haptic portion by a predetermined distance, the lens optic portion and the lens haptic portion being connected together by at least one flexible or resilient arm.

A thirteenth object is to provide an accommodating artificial ocular lens (AAOL) including a lens optic portion connected to a lens plate haptic portion, the lens optic portion being connected to said lens plate portion in a manner so that said lens optic portion tilts relative to a central optical axis of the eye when moved by said lens plate haptic portion during accommodation of the eye.

A fourteenth object is to provide an accommodating artificial ocular lens (AAOL) including a multi-focal lens optic.

A fifteenth object is to provide an accommodating artificial ocular lens (AAOL) including a multi-focal lens optic portion connected to a lens haptic portion.

A sixteenth object is to provide an accommodating artificial ocular lens (AAOL) including a multi-focal lens optic portion connected to a lens plate haptic portion.

A seventeenth object is to provide an accommodating artificial ocular lens (AAOL) including a multi-focal lens optic portion connected to a lens haptic portion.

A eighteenth object is to provide an accommodating artificial ocular lens (AAOL) including a multi-focal lens optic portion connected to a lens plate haptic portion.

A nineteenth object is to provide an accommodating artificial ocular lens (AAOL) including a multi-focal lens optic portion connected to a lens plate haptic portion by at least one flexible or resilient lens arm portion.

A twentieth is to provide an artificial ocular lens (AOL) made of an optically clear polyimide material.

A twenty first object is to provide an improved intraocular lens.

A twenty second object is to provide an improved accommodating intraocular lens.

A twenty third object is to provide an intraocular lens comprising or consisting of a lens optic window.

A twenty fourth object is to provide an intraocular lens comprising or consisting of a lens optic configured to provide accommodation of vision of the eye.

A twenty fifth object is to provide an intraocular lens comprising or consisting of a lens optic or lens optic portion comprising a lens optic window configured to provide accommodation of vision of the eye.

A twenty sixth object is to provide an intraocular lens comprising or consisting of a lens optic or lens optic portion comprising a lens optic window portion configured to provide accommodation of vision of the eye.

A twenty seventh object is to provide an intraocular lens comprising or consisting of a lens optic or lens optic portion comprising a centered lens optic window portion configured to provide accommodation of vision of the eye.

An twenty eighth object is to provide an intraocular lens comprising or consisting of a lens optic or lens optic portion comprising a lens optic window, the lens optic window comprising a flat lens optic portion to provide accommodation of vision of the eye.

A twenty ninth object is to provide an intraocular lens comprising or consisting of a lens optic or lens optic portion comprising a lens optic window, the lens optic window comprising a flat lens surface optic portion to provide accommodation of vision of the eye.

A thirtieth object is to provide an intraocular lens comprising or consisting of a lens optic or lens optic portion comprising a lens optic window, the lens optic window comprising zero or near zero refraction of light.

A thirty first object is to provide an intraocular lens comprising or consisting of a lens optic or lens optic portion comprising a lens optic window, the lens optic window comprising a positive lens surface on one side and a negative lens surface on an opposite side.

A thirty second object is to provide an intraocular lens comprising or consisting of a lens optic or lens optic portion comprising a lens optic window, the lens optic window comprising a positive lens surface portion on one side and a negative lens surface portion on an opposite side to zero out the power of the combined lens set.

A thirty third object is to provide an intraocular lens comprising or consisting of a lens optic or lens optic portion comprising a lens optic window, the lens optic window comprising a flat lens optic portion to provide accommodation of vision of the eye.

A thirty fourth object is to provide an intraocular lens comprising or consisting of a lens optic or lens optic portion comprising a lens optic window configured as a center flat circular lens optic portion to provide accommodation of vision of the eye.

A thirty fifth object is to provide an intraocular lens comprising or consisting of a lens optic or lens optic portion comprising a lens optic window, the lens optic window comprising a center flat non-circular lens optic portion to provide accommodation of vision of the eye.

A thirty sixth object is to provide an intraocular lens comprising or consisting of a lens optic or lens optic portion comprising a lens optic window, the lens optic window comprising a diffractive lens.

A thirty seventh object is to provide an intraocular lens comprising or consisting of a lens optic or lens optic portion comprising a lens optic window, the lens optic window comprising a hole or recess to provide accommodation of vision of the eye.

A thirty eighth object is to provide an intraocular lens comprising or consisting of a lens optic or lens optic portion comprising an optical window, the optical window comprising a lens optic through hole to provide accommodation of vision of the eye.

A thirty ninth object is to provide an intraocular lens comprising or consisting of lens optic or lens optic portion including an optical window, the optical window comprising a center lens optic light tunnel to provide accommodation of vision of the eye.

A fortieth object is to provide an intraocular lens comprising or consisting of a lens optic portion including a lens optic window, the lens optic window comprising a non-circular lens optic hole or through hole configured to provide accommodation of vision of the eye.

A forty first object is to provide an intraocular lens comprising or consisting of a lens optic or lens optic portion comprising a lens optic window, the lens optic window configured as a shaped lens optic hole or through hole to provide accommodation of vision of the eye.

A forty second object is to provide an intraocular lens comprising or consisting of a lens optic portion and a lens haptic portion, the lens optic portion comprising a lens optic window configured to provide accommodation of vision of the eye.

A forty third object is to provide an intraocular lens configured to provide static accommodation of vision of the eye.

A forty fourth object is to provide an intraocular lens configured to provide both static and dynamic accommodation of vision of the eye.

A forty fifth object of the present invention is to provide an intraocular lens comprising or consisting of a lens optic or lens optic portion comprising a lens optic window configured to provide static accommodation of vision of the eye.

A forty sixth object is to provide an intraocular lens comprising or consisting of a lens optic portion and a lens haptic portion configured to provide movement between the lens optic portion and lens haptic portion while being implanted in the eye to provide dynamic accommodating of vision of the eye, the lens optic portion including a lens optic window configured to provide static accommodation of the vision of the eye.

A forty seventh object is to provide an intraocular lens comprising or consisting of a lens optic or lens optic portion comprising an optical window configured as a lens optic insert.

A forty eighth object is to provide an intraocular lens comprising or consisting of a lens optic or lens optic portion comprising an optical window configured as a lens optic insert configured to provide accommodation of vision of the eye.

A forty ninth object is to provide an intraocular lens comprising or consisting of a lens optic or lens optic portion comprising an optical tunnel.

A fiftieth object is to provide an intraocular lens comprising or consisting of a lens optic or lens optic portion comprising an optical tunnel configured to provide accommodation of vision of the eye.

A fifty first object is to provide an intraocular lens comprising or consisting of a lens optic or lens optic portion comprising a wave guide.

A fifty second object is to provide an intraocular lens comprising or consisting of a lens optic or lens optic portion comprising a wave guide configured to provide accommodation of vision of the eye.

A fifty third object is to provide an intraocular lens comprising or consisting of a lens optic or lens optic portion comprising an optical fiber.

A fifty fourth object is to provide an intraocular lens comprising or consisting of a lens optic or lens optic portion comprising an optical fiber configured to provide accommodation of vision of the eye.

A fifty fifth object is to provide an intraocular lens comprising or consisting of a lens optic or lens optic portion including a light guide.

A fifty sixth object is to provide an intraocular lens comprising or consisting of a lens optic or lens optic portion comprising a light guide configured to provide accommodation of vision of the eye.

A fifty seventh object is to provide an intraocular lens comprising or consisting of a lens optic comprising a ring-shaped zone.

A fifty eighth object is to provide an intraocular lens comprising or consisting of a lens optic comprising or consisting of a ring-shaped lens surface.

A fifty ninth object is to provide an intraocular lens comprising or consisting of a lens optic comprising or consisting of a ring-shaped lens optic portion.

A sixtieth object is to provide an intraocular lens comprising or consisting of a lens optic comprising or consisting of a ring-shaped pattern.

A sixty first object is to provide an intraocular lens comprising or consisting of a lens optic comprising or consisting of a ring-shaped mark.

A sixty second object is to provide an intraocular lens comprising or consisting of a lens optic comprising or consisting of a ring-shaped printed mark.

A sixty third object is to provide an intraocular lens comprising or consisting of a lens optic comprising or consisting of a ring-shaped lithography mark.

A sixty forth object is to provide an intraocular lens comprising or consisting of a lens optic comprising or consisting of a ring-shaped mark provided on one or both surfaces of the lens optic.

A sixty fifth object is to provide an intraocular lens comprising or consisting of a lens optic comprising or consisting of a ring-shaped mark provided on one or both surfaces of the lens optic.

A sixty sixth object is to provide an intraocular lens comprising or consisting of a lens optic comprising or consisting of a ring-shaped lens optic portion effecting the optical properties or characteristics of the lens optic.

A sixty seventh object is to provide an intraocular lens comprising or consisting of a lens optic window and a ring-shaped lens optic portion.

A sixty eighth object is to provide an intraocular lens comprising or consisting of a lens optic window in combination with the feature(s) set forth in the fortieth thru the forty six object objects above.

The subject matter of this application is directed to an Artificial ocular lens (AOL) device, in particular an accommodating artificial ocular lens (AAOL) device. For example, the present invention is directed to an accommodating artificial ocular lens (AAOL) device for implanting into the posterior chamber of the eye outside the capsular bag (with or without the natural lens removed) and an accommodating artificial ocular lens (AAOL) device for implanting into the capsular bag of the eye, or otherwise an accommodating intraocular lens (AIOL) device.

The accommodating artificial ocular lens (AAOL) device comprises or consists of a moving lens optic portion. Specifically, the lens optic portion is supported for movement by a lens haptic portion. The lens optic portion is moved when the lens haptic portion is bowed or vaulted through used of flexible connecting arms connecting the lens optic portion to the lens haptic portion. The flexible connection arms move the lens optic portion forward and backward along the central focal axis of the eye during the accommodation process. In preferred embodiment, the lens optic portion is provide with at least one toric, multi-focal and/or wavefront features (e.g. modified or customized lens surfaces and/or lens interiors). Thus, the subject matter provides for a moving toric, multi-focal and/or wavefront lens optics (e.g. translational and/or tilting and/or rotating movement of lens optic) providing a combined or even synergistic effect for increasing the extent, amount or degree of accommodation (e.g. less distance of movement required of lens optic to provide same degree of accommodation).

The accommodating artificial ocular lens (AAOL) device comprises or consists of a lens optic portion connected to a lens haptic portion, preferably a lens plate haptic portion. The lens optic portion can be a hard intraocular lens optic made of a hard or non-deformable material (e.g. polymethylmethacrylate (PMMA) or hard type optically clear polyimide), or can be a soft or flexible or deformable intraocular lens optic made of a soft, flexible, resilient, foldable, compressible and/or otherwise a deformable material I, in particular a substantially deformable material (e.g. silicon, collagen-containing polymer, acrylic, polyimide, soft type polyimide, polyether, polyamide, polyester, polysulfone, polyethersulfone and other biological compatible materials of suitable refractive index).

A particularly preferred material for making the artificial ocular lens (AOL) device and accommodating artificial ocular lens (AAOL) device is an optically clear polyimide material having a refractive index of 1.5, more preferably 1.6, and most preferably 1.7 or higher. The polyimide material preferably has an optical transmittance of ninety percent (90%) or higher, a specific gravity of 1.2 (1.4 maximum), a durometer hardness of 40 to 60 shore A, a tensile strength of approximately 750 psi, an elongation of fifty percent (50%), a tear strength of 100 PPI (50 PPI minimum), and a water absorbtion of one percent (1%) maximum with hydrolytic stability. Further, the polyimide material should be foldable (i.e. folded onto itself for 5 minutes and then released), and sterilizable (i.e. not affected by standard 18 hr 8/12 ethylene oxide cycles, or 1 hr standard 250 F autoclave cycles, and medical grade (i.e. not toxic, carcinogenic, or mutagenic).

The lens plate haptic portion is preferably made of a soft, flexible, resilient, foldable, compressible and/or deformable material, and configured to allow the lens plate haptic portion to bow when an inwardly directed force is applied to the edges or edge portions of the lens plate haptic portion and/or pressure is exerted on the back surface of the capsular bag to move the lens optic portion forward to provide accommodation of the eye. The accommodating artificial ocular lens (AAOL) device according to the present invention can be made as a single piece lens (e.g. by molding or machining), or can be made as a multiple-piece lens assembled together (e.g. hard or soft lens optic portion connected to a separate soft or deformable lens plate haptic portion made of a soft, flexible, resilient, foldable, compressible and/or deformable material).

For example, the lens optic portion of the accommodating artificial ocular lens (AAOL) device remains substantially fixed in size and shape (i.e. fixed conformation) after implantation into the eye, and also remains fixed during accommodation. Specifically, the lens optic portion remains in a fixed conformation, and is not itself bent or bowed once implanted in the eye while the lens haptic portion bows to move the lens optic portion. In this fixed lens optic portion conformation or arrangement, the lens optic portion provides stable or fixed optical characteristics or performance while moving or accommodating within the eye. However, it is to be noted that the lens optic portion, in particular for a soft or deformable type accommodating artificial ocular lens (AAOL) according to the present invention, can be substantially deformed, rolled, compressed or folded for insertion through a small incision (i.e. 3.5 mm or less) and then implanted into the eye.

In another example, the lens optic portion can be configured to tilt (e.g. relative to capsular bag and/or lens plate haptic portion) to provide and/or improve accommodation or during accommodation within the eye. Specific, the lens optic portion is configured so that the optical power of the lens optic portion changes with increased angle of tilt from a reference plane set perpendicular relative to the optical axis of the eye. The lens optic portion can be configured so that the power of the lens optic portion is proportional to the angle of tilt, or alternatively, the lens optic portion can be configured so that the power of the lens optic portion changes exponentially to the angel of tilt.

The accommodating artificial ocular lens (AAOL) device comprises or consists of a lens optic portion and a lens haptic portion, preferably a lens plate haptic portion. The lens optic portion is essentially a separate component from the lens haptic portion except for at least one flexible or resilient arm connecting the lens optic portion to the lens haptic portion. Preferably, at least one opening is provided between an outer edge of the lens optic portion and an inner edge of the lens plate haptic portion. More specifically, the lens optic portion is separated from the lens plate haptic portion by a predetermined fixed or varying distance or spacing. In this arrangement, the outer edge of the lens optic portion is able to move substantially freely and independently relative to the inner edge of the lens plate haptic portion except at the point or points of connection with the flexible or resilient arm(s). Preferably the sizing of the haptic is customized to the particular patient's eye.

The accommodating intraocular lens (AIOL) comprises or consists of at least one arm, preferably a flexible or resilient arm connecting the lens optic portion to the lens plate haptic portion. The flexible or resilient arm is configured to move the lens optic portion along the central focus axis of the eye when the lens plate haptic portion is bowed, for example, when the eye exerts an inwardly directed radial force at one or more positions around the outer edge of the lens plate haptic portion. More specifically, the lens optic portion is moved back-and-forth along the central focal axis of the eye for purposes of accommodation for focusing the eye when the lens plate haptic portion is bowed and unbowed. At least one flexible arm allows the outer edge of the lens optic portion to move relative to the inner edge of the lens plate haptic portion, which becomes distorted as the lens plate haptic portion is bowed. In this manner, the at least one flexible or resilient arm undergoes tensile stress, shear stress, pressure, and some tortional stress when the lens plate haptic portion is bowed without breaking or without permanently deforming. Specifically, the stresses are at a level within the at least one flexible or resilient arm when the lens plate haptic portion is bowed so as to not cause plastic deformation of the at least one flexible or resilient arm. Thus, when the force on the outer edge of the lens plate haptic portion is relieved and/or pressure is relieved behind the lens, the stresses within the at least one arm are relieved and causes the lens optic portion to move back to a resting position relative to the eye.

In some examples of the accommodating artificial ocular lens (AAOL) device, the lens optic portion is initially located in the same plane as the lens plate haptic portion. When force is applied to the outer edge of the lens plate haptic portion, the lens plate haptic portion begins to bow and moves the lens optic portion out of the initial reference plane along the central focal axis of the eye. As the lens plate haptic portion bows, it changes shape substantially from a two-dimensional (2-D) configuration to a cupped or bowed three-dimensional (3-D) configuration, and is substantially no longer planar.

The outer periphery or edge portion of the lens plate haptic portion is preferably configured and/or treated to facilitate or enhance anchoring thereof within the eye. Specifically, the lens plate haptic portion can be provided with one or more through holes to allow tissue on either side of the lens plate haptic portion to adhere together in and through the hole. Alternatively, or in addition, the outer edge of the lens plate haptic portion can be provided with scallops, serrations, notches, protrusions, pins, fingers to facilitate tissue adherence thereto.

Further, preferably the outer edges of the lens plate haptic portion is provided with one or more shape edge portions. For example, the lens plate haptic portion is cut by stamping through the thickness of the lens plate haptic portion to form an upper sharp edge and lower sharp edge. The radius of curvature (i.e. bevel or blend) of these sharp edges is preferably twenty-five (25) microns or less, more preferably ten (10) microns or less, and most preferably five (5) microns or less. The sharper the upper and lower outer perimeter edges of the lens plate haptic, the better the lens plate haptic portion prevents the growth of cells onto the lens plate haptic and lens optic portion when the accommodating artificial ocular lens (AAOL) device is implanted in particular into the capsular bag.

The stamp for making the sharp edges of the lens plate haptic portion is preferably diamond polished at the cutting edges to desirably achieve a radius of curvature of twenty-five microns or less.

In some examples of the accommodating artificial ocular lens (AAOL) device, the lens haptic portion is circular-shaped or substantially rectangular shaped. Further, preferably the lens optic portion is centered relative to the shape of the outer periphery of the lens plate haptic portion.

In another example, the accommodating artificial ocular lens (AAOL) device comprises or consists of a lens optic portion located off center in one or both the length and width dimensions of the lens plate haptic (i.e. relative to the outer perimeter shape of the lens plate haptic portion). In this manner the accommodating artificial ocular lens (AAOL) device can be customized to take into account the morphology of the interior of the eye of a particular patient in custom designing and prescribing the particular accommodating artificial ocular lens (AAOL) device for said patient.

In a further example, the accommodating artificial ocular lens (AAOL) device comprises or consists of a pair of flexible or resilient arms connecting the lens optic portion to the lens plate haptic portion, the lengths of the arm portions being the same or different to center or off-center the lens optic portion relative to the central optical axis of the eye. Further, the location of the pair of arm portions can be located along a center axis of the lens optic portion, or can be located off axis again to center or off-center the lens optic portion relative to the central optical axis of the eye.

In an even further example, the accommodating artificial ocular lens (AAOL) device comprises or consists of a lens optic portion connected to a lens plate haptic portion so that the lens optic portion is tilted relative to said lens plate haptic portion or central focal axis to provide accommodation by tilting and untilting of the lens optic portion changing its effective lens power. Specifically, the artificial ocular lens (AAOL) device is configured or designed to purposely tilt the lens optic to continuously increase the lens power linearly or exponentially proportional relative to the increase in tilting angle. For example, in some embodiments, the angle of tilt remains linear or fixed during bowing of the lens haptic portion, and in other embodiments, the angle of tilt progresses or regresses exponentially based on the extent of bowing of the lens haptic portion. In a further embodiment, the lens optic portion is not tilted relative to the central focal axis of the eye initially (e.g. lens optic portion is located in same plane as lens plate haptic portion initially), and then the lens optic portion progressively tilts relative to the central focal axis of the eye as the lens haptic portion is bowed.

As another example, the accommodating artificial ocular lens (AAOL) device comprises or consists of a multi-focal lens optic portion. The multi-focal lens optic portion provides two or more lens power once implanted in the eye (e.g. bifocal, trifocal, four or more lens powers or different power regions or zones).

The accommodating artificial ocular lens (AAOL) device can be configured to replace the natural crystalline lens of the eye (e.g. an accommodating intraocular lens (AIOL) device for implantation into the capsular bag or an accommodating artificial ocular lens (AAOL) device for implantation into the anterior or posterior chamber of the eye outside the capsular bag). Alternatively, the accommodating artificial ocular lens (AAOL) device according to the present invention can be an accommodating refractive correction lens (ARCL) device configured to be implanted into the eye with the natural crystalline lens intact or combined with an implanted intraocular lens (IOL) device as an additional or supplemental lens (i.e. multiple lens system, two lens system, three lens system, four or more lens system).

For example, an accommodating refractive correction lens (ARCL) device can be a soft or deformable phakic accommodating refractive correction lens (pARCL) device (i.e. accommodating refractive correction lens device added to eye having a substantially healthy or fully functioning natural crystalline lens), or an aphakic supplemental accommodating refractive correction lens (ap-sARCL) device (i.e. accommodating refractive correction lens device added to an eye having an implanted IOL) configured to be implanted through a very small incision in the eye (i.e. 2 mm or less, or preferably 1 mm).

As another example, the accommodating refractive correction lens (ARCL) is a soft or deformable anterior chamber phakic accommodating refractive correction lens (ac-pARCL) device or aphakic supplemental accommodating refractive correction lens (ap-sARCL) device configured to be implanted through a very small incision in the eye.

As an even further example, the accommodating artificial ocular lens (AAOL) device is a soft or deformable custom accommodating artificial ocular lens (c-AAOL) device configured to be implanted through a very small incision in the eye.

Specifically, a custom accommodating artificial ocular lens (c-AAOL) device according to the present invention preferably corrects at least two (2), and more preferably at least three (3) visual problems or defects (e.g. accommodating problems, optical problems, power problems, astigmatic problems, refractive problems, tissue problems, impairments, abnormalities, disease or other factors or conditions impairing or negatively affecting a patient's vision). In a preferred embodiment of the custom accommodating artificial ocular lens (c-AAOL) device according to the present invention, a patient's vision may be corrected to 20:20, more preferably to 20:10, and even possibly to 20:7 and/or best correctable vision and the patient regains substantial to complete accommodation of the eye. In a most preferred embodiment, the custom accommodating artificial ocular lens (c-AAOL) device according to the present invention visually or optically corrects, protects, or otherwise overcomes any and all visual problems or defects.

The custom accommodating artificial ocular lens (c-AAOL) device is manufactured or designed after thoroughly examining, measuring and mapping the patient's eye or eye vision. This information is compiled and then processed to custom manufacture or make the custom accommodating artificial ocular lens (c-AAOL) device for the particular patient. For example, the patient's eye is evaluated for power correction, astigmatism correction, abnormal surface correction, abnormal refractive correction, abnormal tissue correction, and disease correction. For example, abnormal surface profiles or blemishes on the front and/or back surface and/or within the cornea and lens (e.g. natural lens or IOL) are analyzed by wavefront mapping and/or topography of the eye, measuring the internal dimensions of the eye, including cornea, anterior chamber, iris, pupil, posterior chamber, capsular bag, retina, to determine the condition of the eye.

The information from the eye examination, measurements and mapping are processed through a mathematical formula or algorithm embodied in a computer program to calculate the biological, chemical, and physical parameters or characteristics of the custom accommodating artificial ocular lens (c-AAOL) device to be manufactured or made. Specifically, the exact lens size, lens thickness, lens length, lens width, optic location, optic shape, material, material physical properties, material chemistry, material surface chemistry, material refractive index, material hardness, material resilience, material elasticity, material finish, front lens surface conformation, back lens surface conformation, lens curvature, and other processing factors or parameters are determined, and then transformed into machine language for controlling highly precise and accurate computer operated manufacturing equipment (e.g. digitally operated tools) such as lathes, mills, grinding machinery, laser, surface finishing machinery, or any other type of machinery or processes that can be computer operated and controlled for cutting the custom accommodating artificial ocular lens (c-AAOL) device or for cutting a mold for making the custom accommodating artificial ocular lens (c-AAOL) device As another example, the custom accommodating artificial ocular lens (c-AAOL) device can be configured to adjust the overall or macro power of the eye and corrects the astigmatism of the eye. Specifically, the lens optic portion is provided with 1) a lens optic portion for changing the overall or macro power of the eye; and 2) a lens optic portion for correction astigmatism of the eye. For example, the power correction of the lens optic portion can be obtained by cutting or contouring the main overall or macro shape and thickness of the lens optic portion and/or the lens optic portion can be made multi-focal. The lens optic portion can be multi-focal by providing one or both surfaces of the lens optic portion with a multi-focal surface(s). The astigmatic correction of the lens optic portion can be obtained by providing a toric lens optic portion and/or by tilting (i.e. fixed or permanent tilt and/or varying tilting) of the lens optic portion. For example, one or both surfaces of the lens optic portion is provided with toric surfaces.

In a further example, the custom accommodating artificial ocular lens (c-AAOL) device adjusts the power of the eye, corrects the astigmatism of the eye, and corrects the fine or micro optics of eye based on wavefront analysis and mapping of the eye. For example, the power correction of the lens optic portion can be obtained by cutting or contouring the main overall or macro shape and thickness of the lens optic portion and/or the lens optic portion can be made multi-focal refractive and/or diffractive. The astigmatic correction of the lens optic portion can be obtained by providing a toric and/or diffractive lens optic portion. For example, one or both surfaces of the lens optic portion can be made with toric surfaces. Further; the lens optic portion can be made to provide point-to-point optical modification, adjustment, change or fine tuning of the structure and/or shape of the lens optic portion throughout the three dimensions (3-D) of the lens optic portion to micro fine tune or make micro modifications, micro adjustments or micro changes to the lens optic portion on a micro basis to eliminate any and all optical aberrations and provide for full wavefront optical corrections.

In a even further example, the custom accommodating artificial ocular lens (c-AAOL) device according to the present invention includes macro power adjustment, micro power adjustment, multi-focal, toric, and wavefront optics adjustment or correction on one or both sides of the accommodating (i.e. moving) lens optic, and/or within the interior of the accommodating (i.e. moving) lens optic portion.

The accommodating artificial ocular lens (AAOL) device can be custom made to correct any and all vision or optical problems or defects of the eye, including power correction, astigmatism correction, corneal surface and interior aberrations, lens surface and interior aberrations (natural or replacement lens, IOL), and other optical aberrations from other eye structure, eye aqueous and/or eye vitreous. In order to provided a custom accommodating artificial ocular lens (c-AAOL) device, it is required that the vision or optical defects of the eye are carefully measured, for example, by a visual field analyzer, slit lamp, biomicroscope and opthalmoscope. The goal is to provide an accurate and precise "eye assessment" to correct macro vision or optical defects or problems, and micro vision or optical defects or problems such as higher-order aberrations. The wavefront analysis based on adaptic measures of light deviations and aberrations can be measured to 0.01 microns (.mu.m) equivalent to approximately 0.001 diopter (D) adjustment by root mean square deviations (RMS units). Standard refraction methods are used to measure macro visual or optical defects or problems such as low-order aberrations (second-order sphere or defocus and cylinder in 0.25 diopter (D) steps. Up to twenty percent (20%) of the higher-order aberrations come from the corneal, aqueous, lens, and/or vitreous accounting for numerous changes in the indices of refraction of light rays moving through the eye.

The higher-order aberrations require measuring equipment exceeding standard or conventional refractive measuring instruments. The higher-order aberrations include coma (third-order), trefoil (third-order), spherical aberrations and quadra foil (fourth-order), and irregular astigmatism (fifth-order to eighth-order). These higher-order aberrations provide refractive abnormalities well below 0.25 diopter (D unit) translating to three microns (.mu.m) of tissue change within the eye. The wavefront analysis and mapping desired utilizes adaptive optics for measuring root mean square deviation (RMS) using measuring sensors such as a deformable "lenslent" systems to calculate RMS coefficients. The RMS coefficients are then converted into a polynomial pyramid (e.g. Zerneky Pyramid). The three dimensional (3-D) models or two dimensional (2-D) color maps indicate lower and higher order aberrations of the eye. The Zerneky polynomial measure aberrations up to the eleventh (11th) order, and can virtually analyze a hundred percent (100%) of the aberrations of the eye. Above the sixth (6th) order, only noise is created. Point spread functions (PSF) are used to measure and assess higher-orders aberrations in the human vision. These higher-order aberrations include distortions, haloes, tails, and/or double (overlapping) images.

The custom accommodating artificial ocular lens (c-AAOL) device can be made by selecting a material capable of being machined, and then cutting or contouring the front and back surface of the lens optic portion from a blank using a digital lathe, digital mill, laser, or by use of microlithography and/or etching to form or make lens structure or markings. For materials that can be molded, the lens optic portion can be made by machining and polishing a mold cavity, and then molding the lens from a desired material. In an example, the lens mold utilizes a replaceable insert, in particular a replaceable molding pin for molding the lens optic portion of the lens. In this manner, the molding pin can be replaced each time a lens is molded to make a one of a kind custom lens optic portion for a particular patient. The remaining portions of the mold (e.g. to mold plate haptic portion) can be of a standard size and shape, and otherwise not customized.

The molding pin for molding the lens optic portion of the custom accommodating artificial ocular lens (c-AAOL) device can be made by machining the molding pin surface thereof, and then highly polishing the molding pin surface. In a more preferred embodiment, the surface of the molding pin is machined, and then treated to provide a thin metal oxide layer thermally and/or electromagnetically deposited (e.g. vacuum deposited) to eliminate the need for the step of polishing the surface. Specifically, the molding pin is made of a copper/nickel alloy and the molding surface is diamond machined, and then a layer of corundum or aluminum oxide (e.g. sapphire, ruby, diamond (carboneaous)) is vacuum deposited on the molding surface to increase smoothness and durability thereof. The layer is preferably in the thickness range of fifty (50) to four-hundred (400) angstroms (.ANG.).

The custom accommodating artificial ocular lens (c-AAOL) device refractive correction lens can also be used to correct vision or optical defects or problems from prior surgical procedures and/or implants (e.g. after LASIK refractive correction of the cornea and/or after implantation of an IOL).

The subject matter of this application is also directed to an improved intraocular lens, for example, for replacement of the natural crystalline lens and/or an accommodating intraocular lens.

The intraocular lens comprises or consists of a lens optic or lens optic portion. The lens optic can exist by itself, or can be connected to a haptic portion, for example, one or more loop haptic portions or one or more plate haptics portions. The lens optic portion can be hard (e.g. made of hard material, hard plastic, polymethylmethacrylate (PMMA), acrylic, glass, or other biological compatible hard material), or can be deformable or resilient (e.g. made of soft polymer, hydrogel, silicon, collagen based polymer, or other suitable biological compatible materials of suitable refractive index.

The loop haptic, for example, is made of polyester, aramid fiber, or other suitable biocompatible material. The plate haptic portion is preferably made of a substantially flexible or resilient material and configured to allow the plate haptic to deform, flex, or bow when forces and/or pressures are applied by the eye onto the intraocular lens.

The intraocular lens or accommodating intraocular lens can be made as a single piece lens (e.g. by molding or machining), or can be made as a multiple-piece lens assembled together (e.g. hard or soft lens optic portion and resilient or deformable lens haptic portion).

The lens optic or lens optic portion of the intraocular lens or accommodating intraocular lens device can remain stable (e.g. substantially fixed in shape and size after implantation). Specifically, the lens optic or lens optic portion can remain in the same conformation, and is not deformed, bent, or bowed once implanted in the eye. Otherwise, the lens optic portion may not provide consistent light transmission and/or refraction during use or while the accommodating intraocular lens device is performing accommodation within the eye. However, it is to be noted that the lens optic or lens optic portion, in particular for a deformable type intraocular lens or accommodating intraocular lens, can be substantially deformed, rolled or folded during insertion, for example, through a small incision for implantation of the lens device into the eye. This type of lens then regains its operational shape and size, unrolls, or unfolds within the eye for placement in the appropriate position within the eye.

The intraocular lens or accommodating intraocular lens in one embodiment comprises or consists of a lens optic window, in particular a lens optic window configured to provide accommodation of vision of the eye. The lens optic window, for example, is located in the lens optic or lens optic portion of the intraocular lens. Once implanted, this type of intraocular lens provides for "static" accommodation of vision of the eye, since the intraocular lens itself, or parts or portions of the intraocular lens do not have to move relative to each other when implanted in the eye to still provide accommodation of vision of the eye.

The lens optic window (light window) is configured to allow for most light (i.e. light rays) to pass through (e.g. pass straight through) the lens optic window with a minimal to none light refraction or distortion.

It is understood that the intraocular lens can still move somewhat in the eye once implanted. For example, an aphakic intraocular lens may move when implanted into the capsular bag due to movement of the capsular bag, and a phakic intraocular lens may move with movement of the natural crystalline lens of the eye. Further, an anterior chamber lens may move very little or not at all. However, accommodation of vision of the eye is still provided based on optical principles seven when the intraocular lens moves slightly or not at all when implanted in the eye.

The lens optic window can be provided in various arrangements or embodiments. For example, in one embodiment the lens optic window comprises a flat lens optic portion provided on one or both sides of the lens optic or lens optic portion. Preferably, a pair of overlapping flat lens optic portions (e.g. flat surfaces) are provided on each side of the lens optic or lens optic portion. The flat lens optic portions can, for example, be flat circular lens optic portions centered and overlapping and of the same size and shape provided on both sides of the lens optic or lens optic portion.

The flat lens optic portion can be provided on one or both sides of the lens optic portion, and can overlap, partially overlap, or not overlap. Further, the shape and size of the flat lens optic portion can vary on one or both sides of the lens optic or lens optic portion. For example, the flat lens optic portion is a flat shaped lens optic portion (e.g. circular-shaped or round, oval, triangle, square, pentagon, hexagon, octagon, star-shaped, gear-shaped).

The flat lens optic portion is configured to allow light to pass more directly through (e.g. straight through) the thickness of the lens optic or lens optic portion (e.g. pass through lens optic or lens optic portion perpendicular relative to a flat surface of the lens optic portion).

The flat lens optic portion(s), for example, can dimensionally be in the range of 0.5 mm to 4 mm, can be in the range of 0.5 mm to 3 mm, can be in the range of 0.5 mm to 2 mm, or can be approximately 1 mm. Further, the flat lens optic portion(s) can be circular and have a diameter(s) in the range of 0.1 mm to 4 mm, can be in the range of 0.5 mm to 3 mm, can be in the range of 0.5 mm to 2 mm, or can be approximately 1 mm.

As another example, the lens optic window comprises a lens optic tunnel (e.g. hole or holes, partial depth holes or recesses, tunnel, through hole, overlapping partial holes or recesses on both sides). Preferably, the lens optic tunnel can be circular-shaped or round, and centered in the lens optic or lens optic portion. The lens optic light tunnel can be provided on one or both sides of the lens optic or lens optic portion, and can overlap, partially overlap, or not overlap. Further, the shape and size of the lens optic light tunnel can vary on one or both sides of the lens optic or lens optic portion. For example, the lens optic light tunnel is specially shaped in two or three dimensions (e.g. circular-shaped or round, oval, triangle, square, pentagon, hexagon, octagon, star-shaped, gear-shaped, cylindrical-shaped, cone-shaped, tapering, funnel shaped, prism shaped).

The lens optic light tunnel is configured to allow light to pass more directly, or directly through the thickness of the lens optic or lens optic portion (i.e. pass through lens optic portion along focal axis or perpendicular to lens optic or lens optic portion surface and without passing through reduced thickness or no lens material).

For example, the lens optic light tunnel can have a width in the range of 0.5 mm to 4 mm, can be in the range of 0.5 mm to 3 mm, can be in the range of 0.5 mm to 2 mm, or can be approximately 1 mm. Further, the lens optic light tunnel can be circular and have a diameter in the range of 0.5 mm to 4 mm, can be in the range of 0.5 mm to 3 mm, can be in the range of 0.5 mm to 2 mm, or can be approximately 1 mm.

As a further example, the lens optic window comprises a flat lens optic portion and a lens optic light tunnel. Preferably, the flat lens optic portion and lens optic light tunnel are circular-shaped or round, and centered on the lens optic or lens optic portion. The flat lens optic portion and/or lens optic light tunnel can be provided on one or both sides of the lens portion, and can overlap, partially overlap, or not overlap, or configured as a through hole. Further, the shape and size of the flat lens optic portion and/or lens optic light tunnel can vary on one or both sides of the lens optic or lens optic portion.

For example, the flat lens optic portion and/or lens optic light tunnel are shaped (e.g. circular-shaped or round, oval, triangle, square, pentagon, hexagon, octagon, star-shaped, gear-shaped). The combination of the flat lens optic portion and lens optic light tunnel are configured to allow light to pass directly through the thickness of the lens optic or lens optic portion (i.e. pass through lens optic or lens optic portion perpendicular to lens optic or lens optic portion surface and travel the least distance through thickness of the lens optic or lens optic portion).

For example, the flat lens optic portion and/or lens optic light tunnel can dimensionally be in the range of 0.5 mm to 4 mm, can be in the range of 0.5 mm to 3 mm, can be in the range of 0.5 mm to 2 mm, or can be approximately 1 mm. Further, the flat lens optic portion and/or the lens optic light tunnel can be circular and have diameters in the range of 0.5 mm to 4 mm, can be in the range of 0.5 mm to 3 mm, can be in the range of 0.5 mm to 2 mm, or can be approximately 1 mm.

As a further example, the lens optic window comprises a lens optic insert. The lens optic insert, for example, can be provided in the lens optic or lens optic portion and configured to provide accommodation of vision of the eye.

For example, the lens optic insert can dimensionally be in the range of 0.5 mm to 4 mm, can be in the range of 0.5 mm to 3 mm, can be in the range of 0.5 mm to 2 mm, or can be approximately 1 mm. Further, the lens optic insert can be circular and have diameters in the range of 0.5 mm to 4 mm, can be in the range of 0.5 mm to 3 mm, can be in the range of 0.5 mm to 2 mm, or can be approximately 1 mm.

As an even further example, the lens optic window comprises a positive lens optic surface on one side of the lens optic and a negative lens optic surface on an opposite side of the lens optic. For example, the positive lens optic surface can cancel out the negative lens optic surface to zero out the lens power.

For example, the lens optic window, or lens optic surfaces, can dimensionally be in the range of 0.5 mm to 4 mm, can be in the range of 0.5 mm to 3 mm, can be in the range of 0.5 mm to 2 mm, or can be approximately 1 mm. Further, the lens optic insert can be circular and have diameters in the range of 0.5 mm to 4 mm, can be in the range of 0.5 mm to 3 mm, can be in the range of 0.5 mm to 2 mm, or can be approximately 1 mm.

As another example, the lens optic window comprises a diffractive lens optic portion.

For example, the lens optic window, or diffractive lens optic portion, can dimensionally be in the range of 0.5 mm to 4 mm, can be in the range of 0.5 mm to 3 mm, can be in the range of 0.5 mm to 2 mm, or can be approximately 1 mm. Further, the lens optic insert can be circular and have diameters in the range of 0.5 mm to 4 mm, can be in the range of 0.5 mm to 3 mm, can be in the range of 0.5 mm to 2 mm, or can be approximately 1 mm.

The intraocular lens or accommodating intraocular lens in an even further embodiment comprises or consists of a lens optic portion and a haptic portion. The lens optic portion can be connected to the lens haptic portion.

The intraocular lens or accommodating intraocular lens can comprise or consist of a movable lens optic portion and a fixed lens haptic portion, preferably a plate lens haptic portion, relative to the eye in particular the inner eye structure. The lens optic portion functions essentially as a separate component relative to the lens haptic portion, except for at least one flexible or resilient arm connecting the lens optic portion to the lens haptic portion. Preferably, at least one opening is provided between an outer edge of the lens optic portion and an inner edge of the plate lens haptic portion. More specifically, the lens optic portion is separated from most of the plate lens haptic portion by a space (e.g. fixed or varying distance). In this arrangement, the outer edge of the lens optic portion is able to move substantially freely and independently relative to the inner edge of the plate lens haptic portion, except at the point or points of connection with the flexible or resilient arm(s).

This embodiment provides for a type of accommodation with movement of the lens optic portion relative to the lens haptic portion. This embodiment can be combined with a flat lens optic portion and/or lens optic light tunnel to provide additional accommodation (i.e. accommodation provide by both static and dynamic arrangements to enhance accommodation effect).

In the accommodative movement embodiment, the intraocular lens or accommodating intraocular lens comprises or consists of at least one arm, preferably a flexible or resilient arm connecting the lens optic portion to the plate lens haptic portion. The flexible or resilient arm is configured to move the lens optic portion along the central focus axis of the eye when the plate lens haptic portion is deformed, flexed, and/or bowed, for example, when the eye exerts inwardly and/or outwardly radial forces at one or more positions around the outer edge of the plate lens haptic portion and/or on the front or back surfaces of the lens. More specifically, the lens optic portion is moved along the central focal axis of the eye for purposes of accommodation for focusing the eye when the plate lens haptic portion is bowed. At least one flexible arm allows the outer edge of the lens optic portion to move relative to the inner edge of the plate lens haptic portion, which becomes distorted as the plate lens haptic portion is bowed. In this manner, the at least one flexible or resilient arm accommodates tensile stress, shear stress and some torsional stress when the plate lens haptic portion is deformed, flexed, and/or bowed without breaking or permanently deforming. Specifically, the stresses are at a level within the at least one flexible or resilient arm when the plate lens haptic portion is deformed, flexed, and/or bowed so as to not cause plastic deformation of the at least one flexible or resilient arm. Thus, when the force on the lens is relieved, the stresses within the at least one arm are relieved and causes the lens optic portion to move back to a resting position relative to the eye.

The accommodative movement, for example, of the lens optic portion is initially located in the same plane as the plate lens haptic portion. When force is applied to the outer edge of the plate lens haptic portion, the plate lens haptic portion begins to bow and moves the lens optic portion out of the initial reference plane along the central focal axis of the eye. As the plate lens haptic portion bows, it changes shape from substantially from a two (2) dimensional configuration to a cupped or bowed three (3) dimensional configuration, and is substantially no longer planar.

The outer periphery or edge portion of the plate lens haptic portion can be configured and/or treated to facilitate or enhance anchoring thereof within the eye. Specifically, the plate lens haptic portion can be provided with one or more through holes to allow tissue on either side of the plate lens haptic portion to adhere together in the through hole. Alternatively, or in addition, the outer edge of the lens plate haptic portion can be provided with surface treatment (e.g. porous), scallops, serrations and/or notches to facilitate tissue adherence thereto.

In the accommodating intraocular lens, the lens optic portion can be circular shaped or oval shaped. Further, the lens optic portion can be centered relative to the shape of the outer periphery of the plate lens haptic portion.

As an alternative embodiment, the lens optic portion can be located off centered in one or both the length and width dimensions relative to the outer perimeter of the plate lens haptic portion. In this manner, the accommodating intraocular lens device can be customized to take into account the morphology of the interior structure of the eye of a particular patient in custom designing and prescribing the particular accommodating intraocular lens device for the particular patient.

The accommodating intraocular lens can have a pair of flexible or resilient arms connecting the lens optic portion to the plate lens haptic portion, the lengths of the arm portions can be the same or different. Further, the location of the pair of arm portions can be located along a center axis of the lens optic portion or can be located off axis.

As another example, the intraocular lens comprises or consists of a lens optic comprising or consisting of a ring-shaped lens optic portion. The ring-shaped lens optic portion can be configured to effect the optical properties or characteristic of the lens optic. For example, the ring-shaped lens optic portion is configured to block light transmitting through the ring-shaped portion, change the refractive properties of the lens optic, provide a diffractive lens portion(s), and/or provide a multi-focal lens portion(s).

The ring-shaped lens optic portion can be a ring-shaped mark(s) and/or a ring-shaped pattern provided on one or both surfaces of the lens optic.

As a further example, the intraocular lens comprises or consists of a lens optic window and a ring-shaped lens optic portion. The various examples of the lens optic window can be combined with the various examples of the ring-shaped lens optic portion to achieve a variety of optical properties and characteristics of the lens optic and intraocular lens.

BRIEF DESCRIPTION OF THE DRAWINGS

FIG. 21 is a perspective view of an accommodating artificial ocular lens (AAOL) device according to the present invention having double lens optic portions.

FIG. 22 is a center cross-sectional view of the accommodating artificial ocular lens (AAOL) device shown in FIG. 21.

FIG. 23 is a top planar view of the accommodating artificial ocular lens (AAOL) device shown in FIG. 2 in a resting or unstressed condition.

FIG. 24 is a center cross-sectional view of the accommodating artificial ocular lens (AAOL) device, as indicated in FIG. 23.

FIG. 25 is a center cross-sectional view of the accommodating artificial ocular lens (AAOL) device shown in FIG. 24 in a stressed condition showing the lens plate haptic portion bowing and the lens optic portion moving along the optical axis Z of the eye.

FIG. 26 is a center cross-sectional view of the accommodating artificial ocular lens (AAOL) device as indicated in FIG. 23, along the transverse axis Y.

FIG. 53 is a top planar view of an even further embodiment of the accommodating artificial ocular lens (AAOL) device according to the present invention.

FIG. 54 is a side elevational view of the embodiment shown in FIG. 53.

FIG. 55 is a perspective view of another even further embodiment of the accommodating ocular lens (AAOL) device according to the present invention.

FIG. 56 is a side elevational view of the embodiment shown in FIG. 55.

FIG. 77 is a perspective view of an accommodating intraocular lens device having double lens portions.

FIG. 78 is a center cross-sectional view of the accommodating intraocular lens shown in FIG. 21.

FIG. 79 is a top planar view of the lens shown in FIG. 2 in a resting or unstressed condition.

FIG. 80 is a center cross-sectional view of the accommodating intraocular lens, as indicated in FIG. 23.

FIG. 81 is a center cross-sectional view of the accommodating intraocular lens shown in FIG. 24 in a stressed condition showing the plate lens haptic portion bowing and the lens optic portion moving along the optical axis Z of the eye.

FIG. 82 is a center cross-sectional view of the accommodating intraocular lens as indicated in FIG. 23, along the transverse axis Y.

FIG. 83 is a perspective view of an embodiment of the accommodating intraocular lens comprising or consisting of a lens optic window comprising a flat lens optic portion provided in the lens optic portion.

FIG. 84 is a top planar view of the accommodating intraocular lens shown in FIG. 27.

FIG. 85 is a side elevational of the accommodating intraocular lens shown in FIG. 27.

FIG. 86 is a top planer view of an embodiment of the accommodating intraocular lens comprising or consisting of a lens optic window comprising a raised flat lens optic portion provided in the lens optic portion.

FIG. 87 is a side elevational view of the accommodating intraocular lens shown in FIG. 30.

FIG. 88 is a top planar view of an embodiment of the accommodating intraocular lens comprising or consisting of a lens optic window comprising a hole provided in the lens optic portion.

FIG. 89 is a side elevational view of the accommodating intraocular lens shown in FIG. 32.

FIG. 90 is a top planar view of an accommodating intraocular lens comprising or consisting of a lens optic window comprising a tapering hole provided in the lens optic portion.

FIG. 91 is a side elevational view of the accommodating intraocular lens shown in FIG. 34.

FIG. 103 is a center cross-sectional view of an accommodating intraocular lens comprising or consisting of a lens optic window comprising a partial inwardly tapering hole raised flat lens optic portion provided in the lens optic portion.

FIG. 104 is a center cross-sectional view of an accommodating intraocular lens comprising or consisting of a lens optic window comprising a tapering lens optic insert provided in the lens optic portion.

FIG. 105 is a center cross-sectional view of an accommodating intraocular lens comprising or consisting of a lens optic window comprising a pair of outwardly tapering lens optic inserts provided in the lens optic portion.

FIG. 106 is a center cross-sectional view of an accommodating intraocular lens comprising or consisting of a lens optic window comprising an outwardly tapering lens optic insert provided in the lens optic portion.

FIG. 107 is a center cross-sectional view of an accommodating intraocular lens comprising or consisting of a lens optic window comprising a bundled fiber optic lens optic insert provided in the lens optic portion.

FIG. 108 is a center cross-sectional view of an accommodating intraocular lens comprising or consisting of a lens optic window comprising a positive lens optic surface portion and a negative lens optic surface portion.

FIG. 109 is a center cross-sectional view of an accommodating intraocular lens comprising or consisting of a lens FIG. 110 is a center cross-sectional view of an accommodating intraocular lens comprising or consisting of a lens optic window comprising a negative lens optic surface portion and a positive lens optic surface portion.

FIG. 111 is a center cross-sectional view of an accommodating intraocular lens comprising or consisting of a lens optic window comprising a diffractive lens portion.

FIG. 112 is a perspective view of an intraocular lens comprising or consisting of an lens optic comprising or consisting of a ring-shaped lens optic portion and a lens optic window.

FIG. 113 is a top planar view of the intraocular lens shown in FIG. 112.

FIG. 114 is a perspective view of an intraocular lens comprising or consisting of an lens optic comprising or consisting of a ring-shaped lens optic portion and a lens optic window.

FIG. 115 is a top planar view of the intraocular lens shown in FIG. 114.

Figure 116:
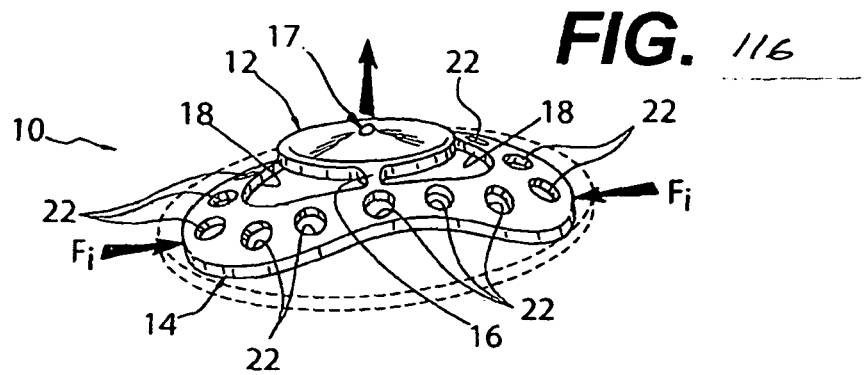

FIG. 116 is a perspective view of another accommodating intraocular lens according to the present invention.

Figure 117:
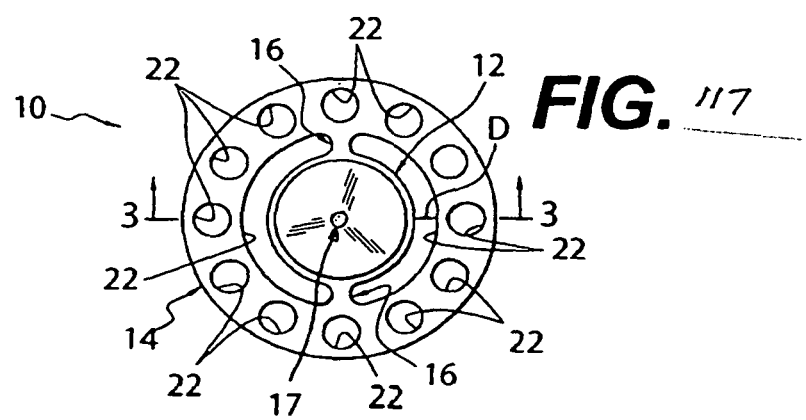

FIG. 117 is a top planar view of the accommodating intraocular lens according to the present invention, as shown in FIG. 116.

Figure 118:
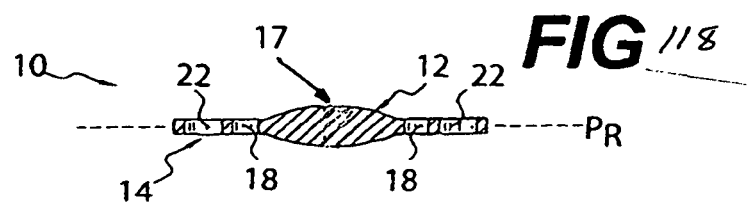

FIG. 118 is a cross-sectional view of the accommodating intraocular lens according to the present invention, as shown in FIG. 116.

Figure 119:
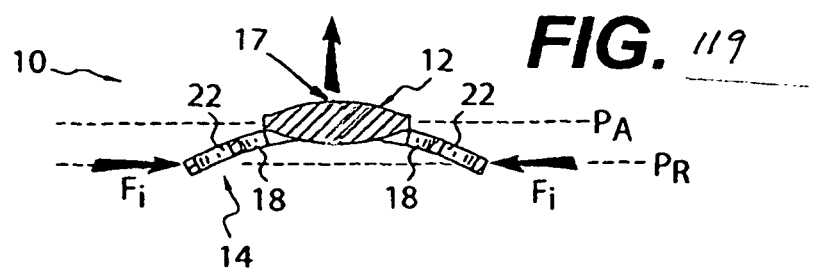

FIG. 119 is a cross-sectional view of the accommodating intraocular lens according to the present invention, as shown in FIG. 116, in an accommodating mode.

DETAILED DESCRIPTION OF PREFERRED EMBODIMENTS

A preferred embodiment of a deformable accommodating artificial ocular lens (A/AOL) device 10 according to the present invention is shown in FIGS. 1 to 4.

Figure 2:
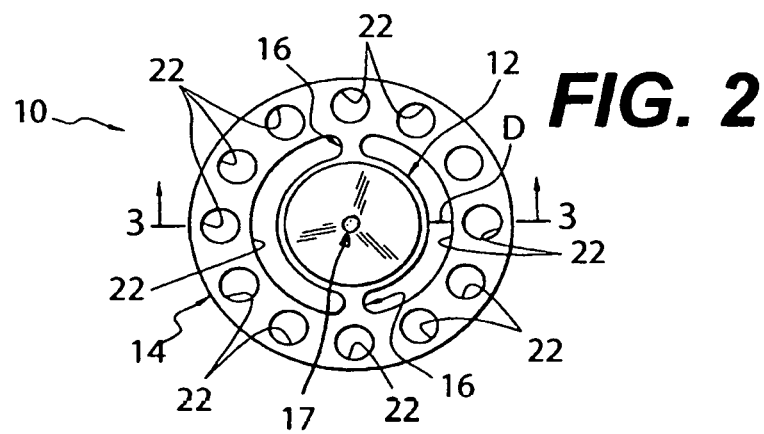
FIG. 2 is a top planar view of the deformable accommodating artificial ocular lens (AAOL) device, as shown in FIG. 1.
Figure 3:
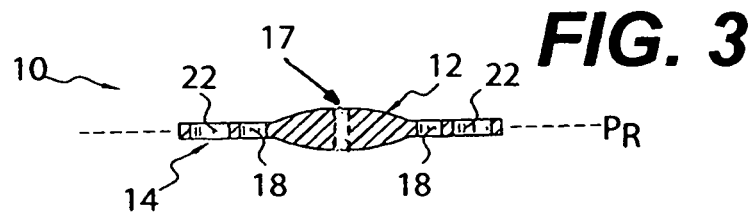
FIG. 3 is a cross-sectional view of the deformable accommodating artificial ocular lens (AAOL) device, as indicated in FIG. 2, in an unstressed condition.
Figure 4:
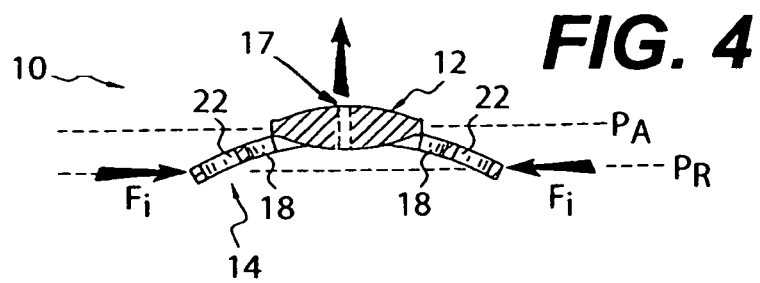
FIG. 4 is a cross-sectional view, as shown in FIG. 3, when the accommodating artificial ocular lens (AAOL) device is in a stressed condition.

The deformable accommodating artificial ocular lens (AAOL) device 10 includes a lens optic portion 12 and a lens plate haptic portion 14. The lens optic portion 12 is connected to the lens plate haptic portion 14 by a pair of flexible or resilient lens arm portions 16, 16, as shown in FIG. 2. A pair of partial circular-shaped lens openings 18, 18 separate the lens optic portion 12 from the lens plate haptic portion 14, as shown in FIG. 2, by a predetermined distance D. In this manner, the lens optic portion 12 is structurally substantially independent of lens plate haptic portion 18, except at the two (2) points of connection provided by the resilient or flexible lens arm portions 16, 16.

The perimeter of the lens plate haptic portion 14 is provided with a plurality of lens through holes 22 to facilitate adherence of tissue through the lens through holes 22 by tissue located on either side of the perimeter of the lens plate haptic portion 14 connecting together in and through the lens through holes 22. In this manner, once the deformable accommodating artificial ocular lens (AAOL) device 10 has been implanted and the eye has healed, the perimeter of the lens plate haptic portion 14 becomes substantially anchored in place.

In the preferred embodiments shown in FIGS. 1 to 4, the lens optic portion 12, lens plate haptic portion 14 and lens arm portions 16, 16 are made together as a one-piece unitary structure from soft, flexible, resilient, foldable, compressible or deformable polymer material (e.g. by molding or machining a single piece of stock material). The deformable accommodating artificial ocular lens (AAOL) device 10 can be inserted through a small incision (e.g. 2.0 mm or less) through the cornea of the eye in a deformed rolled, folded or otherwise compressed condition by use of forceps or a lens injecting device.

Figure 5:
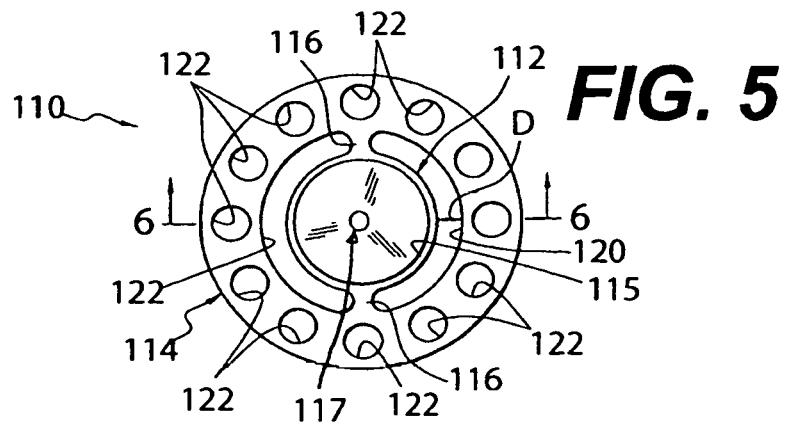
FIG. 5 is a top planar view of another embodiment of the accommodating artificial ocular lens (AAOL) device according to the present invention.
Figure 6:
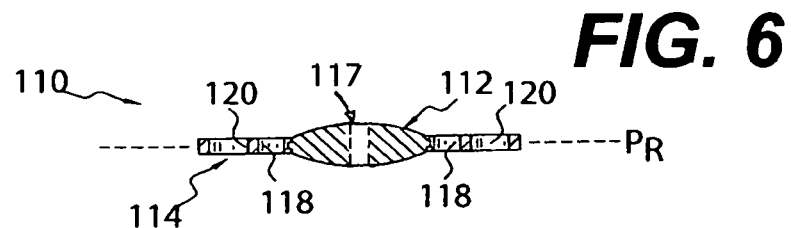
FIG. 6 is a cross-sectional view of the artificial ocular lens (AAOL) device as indicated in FIG. 5.
Figure 7:
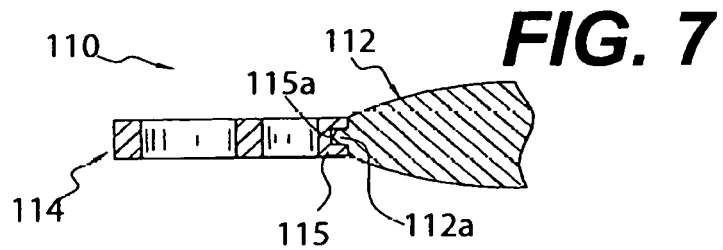
FIG. 7 is a partial broken away detailed cross-sectional view of a portion of the accommodating artificial ocular lens (AAOL) device shown in FIGS. 5 and 6.

Another embodiment of a partially deformable accommodating artificial ocular lens (AAOL) device 110 is shown in FIGS. 5-7.

The partially deformable accommodating artificial ocular lens (AAOL) device 110 includes a lens optic portion 112 and a lens plate haptic portion 114. The lens optic portion 112 is connected to the lens plate haptic portion 114 by a pair of resilient or flexible lens arm portions 116.

In this particular preferred embodiment, the lens optic portion 112 is made out of non-resilient or non-deformable material such as polymethyl methacrylate or hard type polyimide. However, the plate haptic portion 114 is made from a resilient polymer material and the partially deformable accommodating artificial ocular lens (AAOL) device 110 is made from two (2) separate pieces and assembled together to become a single piece accommodating artificial ocular lens (AAOL) device. Further, the accommodating artificial ocular lens (AAOL) device according to the present invention can be made of a material that varies in hardness or stiffness along its length (e.g. harder lens optic portion and softer lens plate haptic portion, or reverse).

The lens plate haptic portion 114 includes a resilient lens carrier or lens receiving portion 115 provided with an inner groove 115a cooperating with a tongue portion 112a of the lens optic portion 112 as shown in FIG. 7. The lens optic portion 112 can be secured in place due to the resilient nature of the lens receiver or lens carrier 115 of the lens plate haptic portion 114 due to its capacity to withstand a certain amount of band stress. Alternatively, or in addition, the tongue portion 112a can be adhered by glue, adhesive, welding or other technique to secure the lens optic portion 112 to the lens receiver or lens carrier 115 of the lens plate haptic portion 114.

The partially deformable accommodating artificial ocular lens (AAOL) device is inserted through a relatively large incision made in the cornea by forceps and then implanted into the capsular bag after cataract lens removal.

Figure 8:
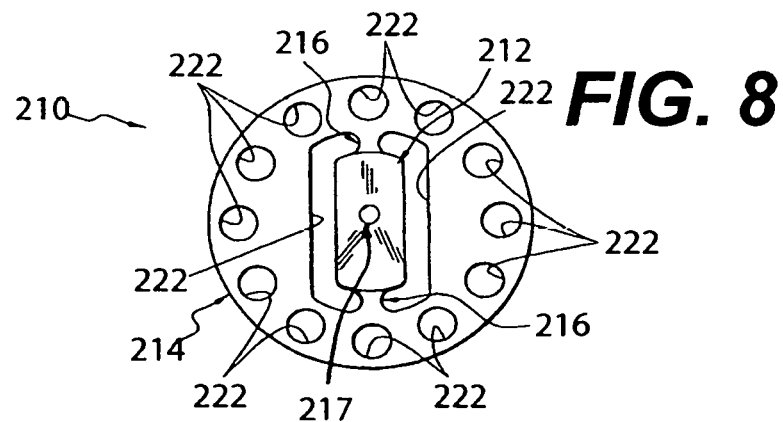
FIG. 8 is a top planar view of another embodiment of an accommodating artificial ocular lens (AAOL) device according to the present invention.

A further embodiment of the accommodating artificial ocular lens (AAOL) device 210 according to the present invention is shown in FIG. 8.

The accommodating artificial ocular lens (AAOL) device 210 includes a substantially rectangular lens optic portion 212 connected to a round-shaped lens plate haptic portion 214 by a pair of flexible or resilient lens arm portions 216, 216. A pair of oblong or partially oval-shaped or arc-shaped lens openings 220, 220 are provided between the lens optic portion 212 and the lens plate haptic portion 214. A plurality of lens through holes 222 are provided to facilitate anchoring of the perimeter of the lens plate haptic portion 214.

Figure 9:
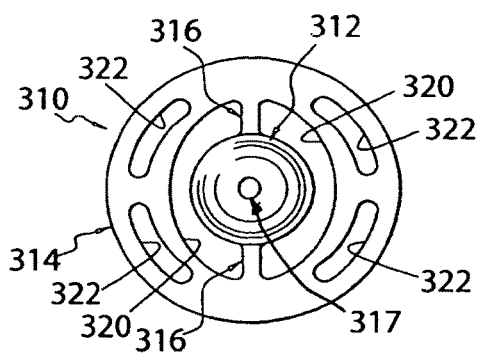
FIG. 9 is a top planar view of another embodiment of an accommodating artificial ocular lens (AAOL) device according to the present invention.

A further embodiment of the accommodating artificial ocular lens (AAOL) device 310 according to the present invention is shown in FIG. 9.

The accommodating artificial ocular lens (AAOL) device 310 includes a substantially round lens optic portion 312 connected to a round-shaped lens plate haptic portion 314 by a pair of flexible or resilient lens arm portions 316, 316. A pair of oblong or partially oval-shaped or arc-shaped lens openings 320, 320 are provided between the lens optic portion 312 and the lens plate haptic portion 314. A plurality of lens through holes 322 are provided to facilitate anchoring of the perimeter of the lens plate haptic portion 314.

Figure 10:
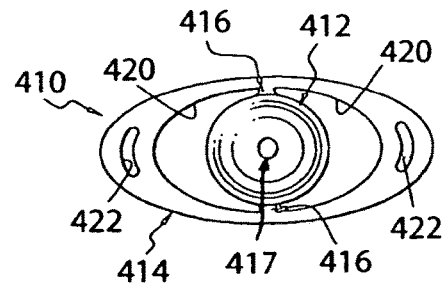
FIG. 10 is a top planar view of another embodiment of an accommodating artificial ocular lens (AAOL) device according to the present invention.

A further embodiment of the accommodating artificial ocular lens (AAOL) device 410 according to the present invention is shown in FIG. 10.

The accommodating artificial ocular lens (AAOL) device 410 includes a substantially round-shaped lens optic portion 412 connected to an oblong-shaped or oval-shaped or arc-shaped lens plate haptic portion 414 by a pair of flexible or resilient lens arm portions 416, 416. A pair of oblong or partial oval-shaped or arc-shaped lens openings 420, 420 are provided between the lens optic portion 412 and the lens plate haptic portion 414. A plurality of lens through holes 422 are provided to facilitate anchoring of the perimeter of the lens plate haptic portion 414.

Figure 11:
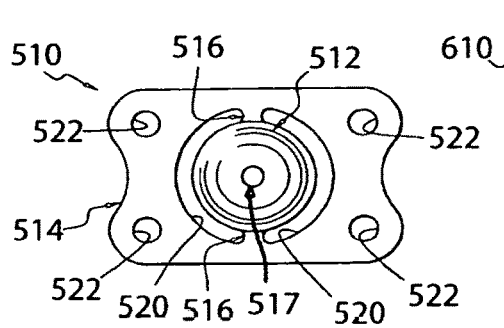
FIG. 11 is a top planar view of another embodiment of an accommodating artificial ocular lens (AAOL) device according to the present invention.

A further embodiment of the accommodating artificial ocular lens (AAOL) device 510 according to the present invention is shown in FIG. 11.

The accommodating artificial ocular lens (AAOL) device 510 includes a round-shaped lens portion 512 connected to a modified oblong-shaped or substantially rectangular-shaped lens plate haptic portion 514 by a pair of flexible or resilient lens arm portions 516, 516. A pair of oblong or partial oval-shaped lens openings 520, 520 are provided between the lens optic portion 512 and the lens plate haptic portion 514. A plurality of lens through holes 522 are provided to facilitate anchoring of the perimeter of the lens plate haptic portion 514.

Figure 12:
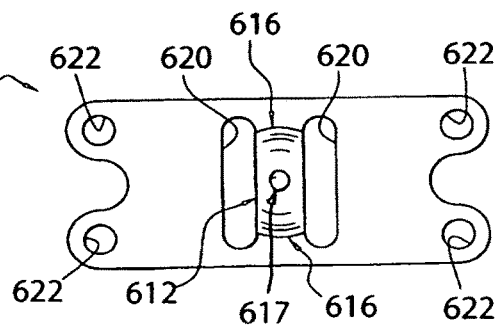
FIG. 12 is a top planar view of another embodiment of an accommodating artificial ocular lens (AAOL) device according to the present invention.

Another embodiment of the accommodating artificial ocular lens (AAOL) device 610 according to the present invention is shown in FIG. 12.

The accommodating artificial ocular lens (AAOL) device 610 includes an elongated lens optic portion 612 connected to an elongated lens plate haptic portion 614 by a pair of flexible or resilient lens arm portions 616, 616. A pair of oblong-shaped or oval-shaped or arc-shaped lens openings 620, 620 are provided between the lens optic portion 612 and the lens plate haptic portion 614. A plurality of lens through holes 622 are provided to facilitate anchoring of the ends of the lens plate haptic portion 614 in the eye.

Figure 13:
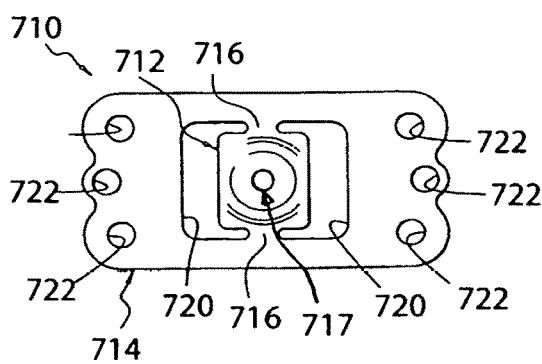
FIG. 13 is a top planar view of another embodiment of an accommodating artificial ocular lens (AAOL) device according to the present invention.

A further embodiment of the accommodating artificial ocular lens (AAOL) device 710 according to the present invention is shown in FIG. 13.

The accommodating artificial ocular lens (AAOL) device 710 includes a rectangular-shaped lens optic portion 712 connected to a rectangular-shaped lens plate haptic portion 714 by a pair of flexible or resilient lens arm portions 716, 716. A pair of rectangular oval-shaped or arc-shaped lens openings 720, 720 are provided between the lens optic portion 712 and the lens plate haptic portion 714. A plurality of lens through holes 722 are provided to facilitate anchoring of the ends of the lens plate haptic portion 714 within the eye.

Figure 14:
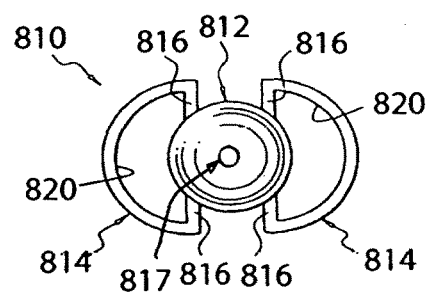
FIG. 14 is a top planar view of another embodiment of an accommodating artificial ocular lens (AAOL) device according to the present invention.

An even further embodiment of the accommodating artificial ocular lens (AAOL) device 810 according to the present invention is shown in FIG. 14.

The accommodating artificial ocular lens (AAOL) device 810 includes a round-shaped lens optic portion 812 connected to a pair of half-circle shaped or arc-shaped lens plate haptic portions 814, 814 each by a pair of flexible or resilient lens arm portions 816, 816. A pair of half-circle shaped or arc-shaped lens openings 820, 820 are provided between the lens optic portion 812 and the lens plate haptic portions 814, 814. In this embodiment, the lens openings 820, 820 also provide the function of lens through holes in previous embodiments to facilitate anchoring the ends of the lens plate haptic portions 814, 814 in the eye.

Figure 15:
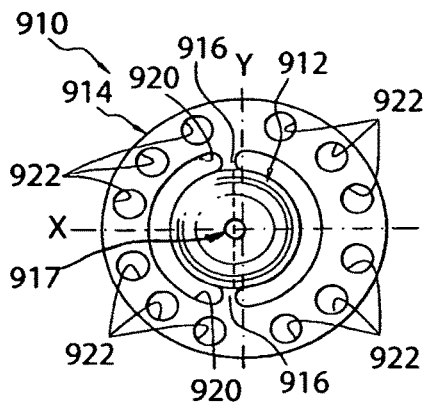
FIG. 15 is a top planar view of another embodiment of an accommodating artificial ocular lens (AAOL) device according to the present invention.

Another embodiment of the accommodating artificial ocular lens (AAOL) device 910 according to the present invention is shown FIG. 15.

The accommodating artificial ocular lens (AAOL) device 910 includes a round-shaped lens optic portion 912 connected to a round-shaped lens plate haptic portion 914 by a pair of flexible or resilient lens arm portions 916, 916. The lens arm portions 916, 916 are approximately the same length. A pair of half circular-shaped or arc-shaped lens openings 920, 920 are provided between the lens optic portion 912 and the lens plate haptic portion 914. A plurality of lens through holes 922 are provided to facilitate anchoring the lens plate haptic portion 914 in the eye. In this embodiment, the lens optic portion 912 is located off-centered along the Y axis making the round-shaped lens plate haptic portion somewhat asymmetrical in shape relative to the X axis.

Figure 16:
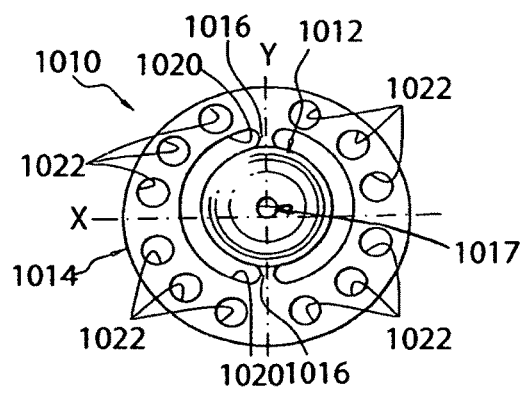
FIG. 16 is a top planar view of a further embodiment of an accommodating artificial ocular lens (AAOL) device according to the present invention.

Another embodiment of the accommodating artificial ocular lens (AAOL) device 1010 according to the present invention is shown in FIG. 16.

The accommodating artificial ocular lens (AAOL) device 1010 includes a round-shaped lens portion 1012 connected to a round-shaped lens plate haptic portion 1014 by a pair of flexible or resilient lens arm portions 1016, 1016. A pair of half circle-shaped lens openings 1020, 1020 are provided between the lens optic portion 1012 and the lens plate haptic portion 1014. A plurality of lens through holes 1022 are provided to facilitate anchoring the perimeter of the lens plate haptic portion 1014 in the eye. In this embodiment, the lens optic portion 1012 is located off-center along the X axis resulting in the lens plate haptic portion 1014 being asymmetrical relative to the Y axis.

Figure 17:
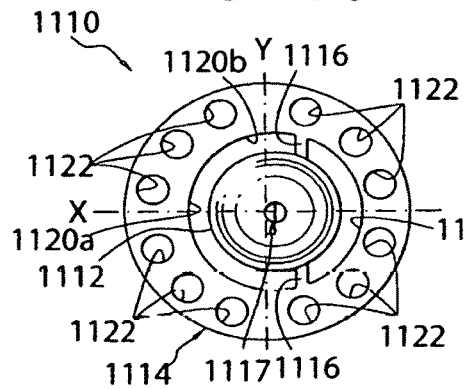
FIG. 17 is a top planar view of a further embodiment of an accommodating artificial ocular lens (AAOL) device according to the present invention.

Another embodiment of the accommodating artificial ocular lens (AAOL) device 1110 according to the present invention is shown in FIG. 17.

The accommodating artificial ocular lens (AAOL) device 1110 includes a round-shaped lens portion 1112 connected to a round-shaped lens plate haptic portion 1114 by a pair of flexible or resilient lens arm portions 1116, 1116. The lens arm portions 1116, 1116 are both located off axis relative to the Y axis. A pair of half circular-shaped lens openings 1120a, 1120b are provided between the lens optic portion 1112 and the lens plate haptic portion 1114. It is to be noted that the lens opening 1120a is larger than the lens opening 1120b. A plurality of lens through holes 1122 are provided to facilitate anchoring of the perimeter of the lens plate haptic portion 1114 in the eye.

Figure 18:
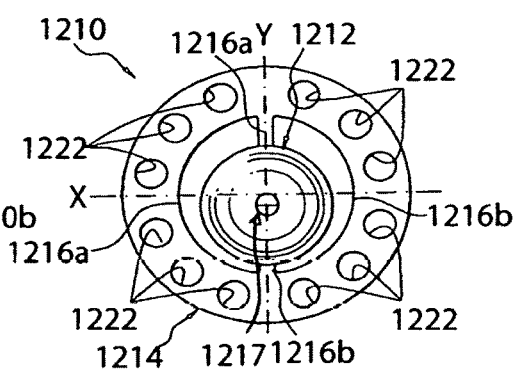
FIG. 18 is a top planar view of another embodiment of an accommodating artificial ocular lens (AAOL) device according to the present invention.

Another embodiment of the accommodating artificial ocular lens (AAOL) device 1210 according to the present invention is shown in FIG. 18.

The accommodating artificial ocular lens (AAOL) device 1210 includes a round-shaped lens optic portion 1212 connected to a round-shaped lens plate haptic portion 1214 by a pair of flexible or resilient lens arm portions 1216a and 1216b. It is to be noted that the lens arm portion 1216a is longer than the lens arm portion 1216b. A-pair of asymmetrical half circular-shaped lens openings 1220 are provided between the lens optic portion 1212 and the lens plate haptic portion 1214. A plurality of lens through holes 1222 are provided to facilitate anchoring of the perimeter of the lens plate haptic portion 1214 in the eye.

Figure 19:
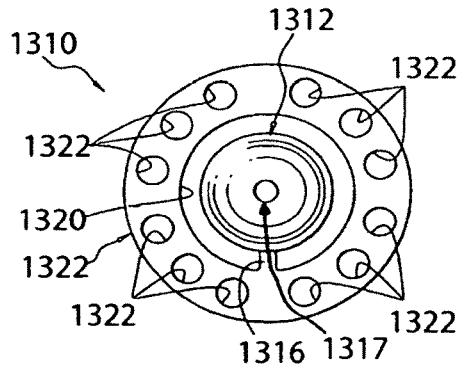
FIG. 19 is a top planar view of a further embodiment of an accommodating artificial ocular lens (AAOL) device according to the present invention.

Another embodiment of the accommodating artificial ocular lens (AAOL) device 1310 according to the present invention is shown in FIG. 19.

The accommodating artificial ocular lens (AAOL) device 1310 includes a round-shaped lens portion 1312 connected to a round-shaped lens plate haptic portion 1314 by a single flexible or resilient lens arm portion 1316. A single circular-shaped lens opening 1320 is provided to separate the lens portion 1312 from the lens plate haptic portion 1314. A plurality of lens through holes 1322 are provided to facilitate anchoring of the perimeter of the lens plate haptic portion 1314 in the eye.

Figure 20:
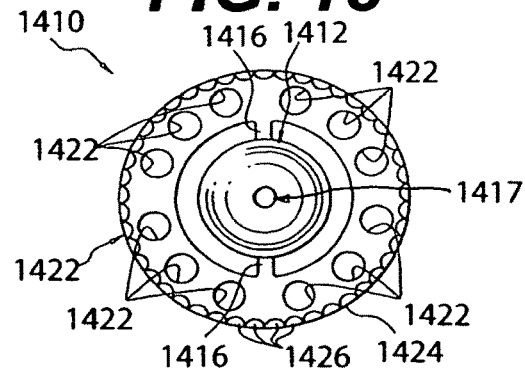
FIG. 20 is a top planar view of a further embodiment of an accommodating artificial ocular lens (AAOL) device according to the present invention.

Another embodiment of the accommodating artificial ocular lens (AAOL) device 1410 according to the present invention is shown in FIG. 20.

The accommodating artificial ocular lens (AAOL) device 1410 includes a round-shaped lens portion 1412 connected to a round-shaped plate haptic portion 1414 by a pair of flexible or resilient lens arm portions 1416, 1416. A pair of half-circle shaped or arc-shaped lens openings 1420, 1420 are provided between the lens optic portion 1412 and the lens plate haptic portion 1414. A plurality of lens through holes 1422 are provided to facilitate anchoring of the perimeter of the lens plate haptic portion 1414 in the eye. In addition, the lens edge 1424 is provided with lens scalloped portions 1426 around the perimeter thereof to facilitate the fibrotic fixation process. Alternatively, or in addition, the lens scalloped portions 1426 can be replaced or augmented with lens edge serrations, notches, protrusions, pins, fingers and/or flaps.

The lens opening in the above-embodiment can be of the same size and/or shape (i.e. symmetrical or mirror-image), or can be of different size and/or shape (i.e. asymmetric) to provide various effects or features customized for a particular patient during accommodation of the lens optic portion.

A double lens optic embodiment of the accommodating artificial ocular lens (AAOL) device 1510 according to the present invention is shown in FIGS. 21 and 22.

The accommodating artificial ocular lens (AAOL) device 1510 includes a front accommodating lens portion 1510a and a back accommodating lens portion 1510b. The lens portion 1510a and the lens portion 1510b are essentially the same configuration except reverse oriented and assembled back-to-back.

The accommodating artificial ocular lens (AAOL) portion 1510a includes a round-shaped lens optic portion 1512a connected to a round-shaped lens plate haptic portion 1514a by a pair of flexible or resilient lens arm portions 1516a, 11516a. A pair of half circular-shaped lens openings 1520a, 1520a are provided between the lens optic portion 1512a and the lens plate haptic portion 1514a. A plurality of lens through holes 1522a are provided to facilitate anchoring of the perimeter of the lens plate haptic portion 1514a in the eye. The accommodating artificial ocular lens (AAOL) portion 1510b is the same or similarly configured to the accommodating artificial ocular lens (AAOL) portion 1510a. As shown in FIG. 22, the outer edges or perimeter of the accommodating artificial ocular lens (AAOL) portions 1510a and 1510b contact or engage each other when implanted in the eye.

The accommodating artificial ocular lens (AAOL) portions 1510a, 1510b can be connected together continuously around the outer perimeter thereof, or can be connected at a number of separate points around the outer perimeter thereof. Further, the accommodating artificial ocular lens (AAOL) portions 1510a, 1510b can be unstressed (i.e. not arched) when assembled together, or can be prestressed (i.e. pre-arched) prior to being assembled together.

A preferred embodiment of the lens plate haptic portion has a length preferably from 8 millimeters to 13 millimeters, a width from 5 to 13 millimeters, and a thickness from 0.05 millimeters to 1 millimeter. The lens opening distance D is preferably 0.20 to 2.0 millimeters. It is important that the ratio of the radial length of the lens plate haptic portion relative to the axial thickness of the lens plate haptic portion is preferably 1.5 to 8 or more, to provide sufficient bowing of the lens plate haptic portion when stressed inwardly by forces applied by the eye.

A variety of different embodiments of the lens optic portion of the accommodating artificial ocular lens (AAOL) device according to the present invention is shown in FIGS. 27A, 27B through FIGS. 43A, 43B.

Figure 27A:
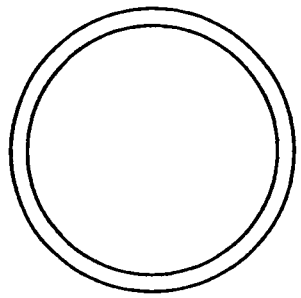
FIG. 27A is a broken away top planar view of the front side of the lens optic portion of the accommodating artificial ocular lens (AAOL) device shown in FIG. 1.
Figure 27B:
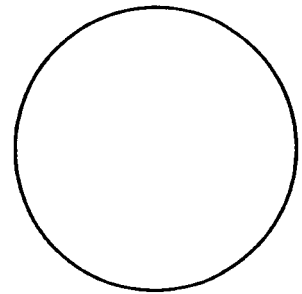
FIG. 27B is a broken away bottom planar view of the back side of the lens optic portion of the accommodating artificial ocular lens (AAOL) device shown in FIG. 1.

In the embodiment shown in FIGS. 27A and B, the front surface of the lens optic portion is provided with front and back optical surface portions configured to provide add or subtract lens power to the eye.

Figure 28A:
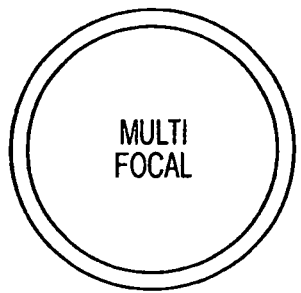
FIG. 28A is a broken away top planar view of the front side of a lens optic portion of a preferred embodiment of the accommodating artificial ocular lens (AAOL) device according to the present invention having a multi-focal front surface portion.
Figure 28B:
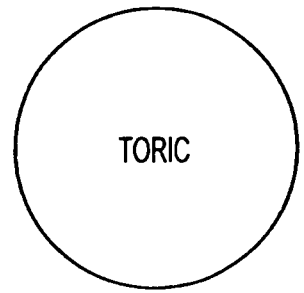
FIG. 28B is a bottom planar view of the back side of the lens optic portion, shown in FIG. 28A, having a toric back surface portion.

In the embodiment shown in FIGS. 28A and B, the front surface of the lens optic portion is provided with a multi-focal front surface portion and the back side of the lens optic portion is provided with a toric back surface portion.

Figure 29A:
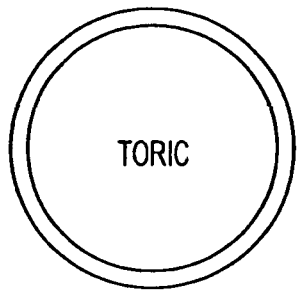
FIG. 29A is a broken away top planar view of the front side of a lens optic portion of a preferred embodiment of the accommodating artificial ocular lens (AAOL) device according to the present invention having a toric front surface portion.
Figure 29B:
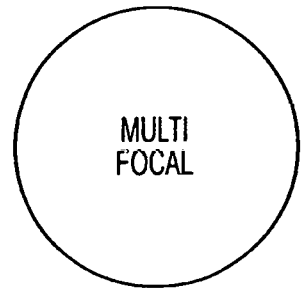
FIG. 29B is a broken away bottom planar view of the back side of the lens optic portion, as shown in FIG. 29A, having a multi-focal back surface portion.

In the embodiment shown in FIGS. 29A and B, the front side of the lens optic portion is provided with a toric front surface portion and the back side of the lens optic portion is provided with a multi-focal back surface portion.

Figure 30A:
FIG. 30A is a broken away top planar view of the front side of a lens optic portion of a preferred embodiment of the accommodating artificial ocular lens (AAOL) device according to the present invention having both a multi-focal and toric front surface portion.
Figure 30B:
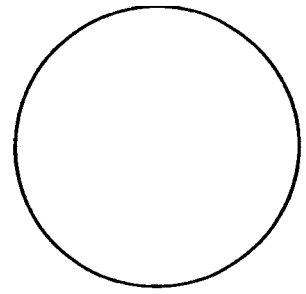
FIG. 30B is a broken away bottom planar view of the back side of the lens optic portion, as shown in FIG. 30A.

In the embodiment shown in FIGS. 30A and B, the front side of the lens optic portion is provided with a both a multi-focal and toric front surface portion and the back side of the lens optic portion is provided with a optical back surface portion.

Figure 31A:
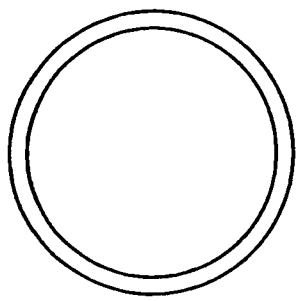
FIG. 31A is a broken away top planar view of the front side of a lens optic portion of a preferred embodiment of the accommodating artificial ocular lens (AAOL) device according to the present invention.
Figure 31B:
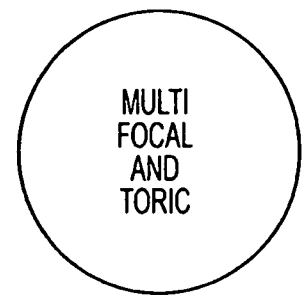
FIG. 31B is a broken away bottom planar view of the back side of the lens optic portion, as shown in FIG. 31A, having both a multi-focal and toric back surface portion.

In the embodiment shown in FIGS. 31A and B, the front side of the lens optic portion is provided with an optical front surface portion and the back side of the lens optic portion is provided with both multi-focal and toric back surface portions.

Figure 32A:
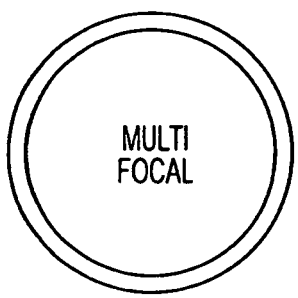
FIG. 32A is a broken away top planar view of the front side of a lens optic portion of a preferred embodiment of the accommodating artificial ocular lens (AAOL) device according to the present invention having a multi-focal front surface portion.
Figure 32B:
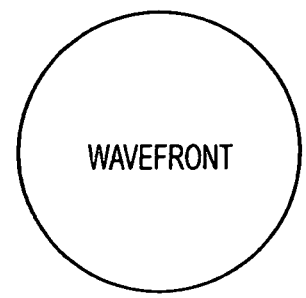
FIG. 32B is a broken away bottom planar view of the back side of the lens optic portion, as shown in FIG. 32A, having a wavefront back surface portion.

In the embodiment shown in FIGS. 32A and B, the front side of the lens optic portion is provided with a multi-focal surface portion and the back side of the lens optic portion is provided with a wavefront back surface portion.

Figure 33A:
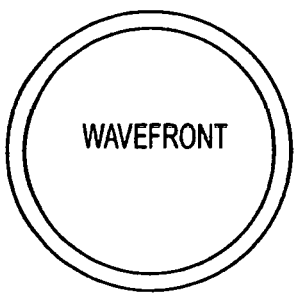
FIG. 33A is a broken away top planar view of the front side of a lens optic portion of a preferred embodiment of the accommodating artificial ocular lens (AAOL) device according to the present invention having a wavefront front surface portion.
Figure 33B:
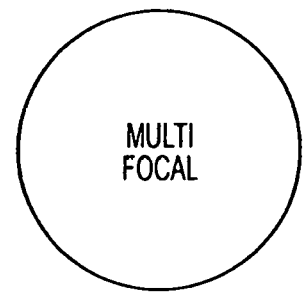
FIG. 33B is a broken away bottom planar view of the back side of the lens optic portion, as shown in FIG. 33A, having a multi-focal back surface portion.

In the embodiment shown in FIGS. 33A and B, the front side of the lens optic portion is provided with a wavefront front surface portion and the back side of the lens optic portion is provided with a multi-focal back surface portion.

Figure 34A:
FIG. 34A is a broken away top planar view of the front side of a lens optic portion of a preferred embodiment of the accommodating artificial ocular lens (AAOL) device according to the present invention having both a multi-focal and wavefront front surface portion.
Figure 34B:
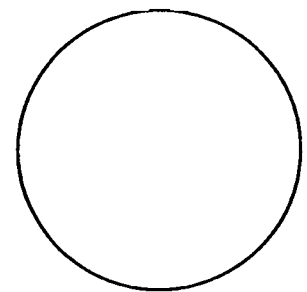
FIG. 34B is a broken away bottom planar view of the back side of the lens optic portion, as shown in FIG. 34A.

In the embodiment shown in FIGS. 34A and B, the front side of the lens optic portion is provided with both a multi-focal and wavefront front surface portion and the back side of the lens optic portion is provided with a optical back surface portion.

Figure 35A:
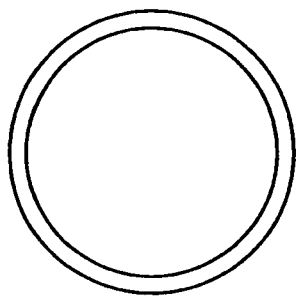
FIG. 35A is a broken away top planar view of the front side of a lens optic portion of a preferred embodiment of the accommodating artificial ocular lens (AAOL) device according to the present invention.
Figure 35B:
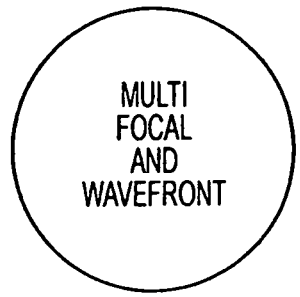
FIG. 35B is a broken away bottom planar view of the back side of the lens optic portion, as shown in FIG. 35A, having both a multi-focal and wavefront back surface portion.

In the embodiment shown in FIGS. 35A and B, the front side of the lens optic portion is provided with an optical front surface portion and the back side of the lens optic portion is provided with both a multi-focal and wavefront back surface portion.

Figure 36A:
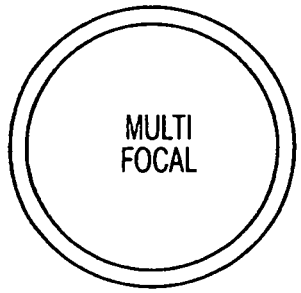
FIG. 36A is a broken away top planar view of the front side of a lens optic portion of a preferred embodiment of the accommodating artificial ocular lens (AAOL) device according to the present invention having a multi-focal front surface portion.
Figure 36B:
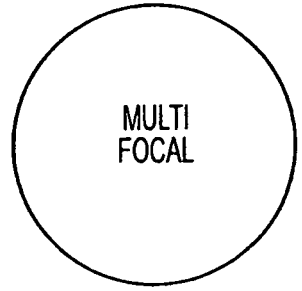
FIG. 36B is a broken away bottom planar view of the back side of the lens optic portion, as shown in FIG. 36A, having a multi-focal back surface portion.

In the embodiment shown in FIGS. 36A and B, the front side of the lens optic portion is provided with a multi-focal front surface portion and the back side of the lens optic portion is provided with a multi-focal back surface portion.

Figure 37A:
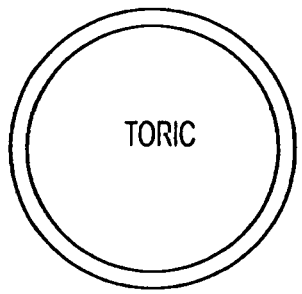
FIG. 37A is a broken away top planar view of the front side of a lens optic portion of a preferred embodiment of the accommodating artificial ocular lens (AAOL) device according to the present invention having a toric front surface portion.
Figure 37B:
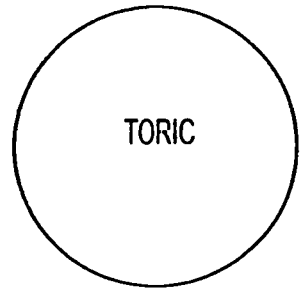
FIG. 37B is a broken away bottom planar view of the back side of the lens optic portion, as shown in FIG. 37A, having a toric back surface portion.

In the embodiment shown in FIGS. 37A and B, the front side of the lens optic portion is provided with a toric front surface portion and the back side of the lens optic portion is provided with a toric back surface portion.

Figure 38A:
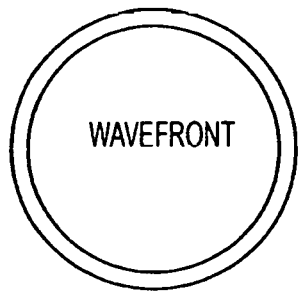
FIG. 38A is a broken away top planar view of the front side of a lens optic portion of a preferred embodiment of the accommodating artificial ocular lens (AAOL) device according to the present invention having a wavefront front surface portion.
Figure 38B:
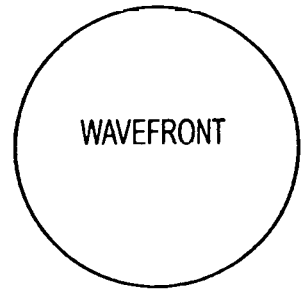
FIG. 38B is a broken away bottom planar view of the back side of the lens optic portion, as shown in FIG. 38A, having a wavefront back surface portion.

In the embodiment shown in FIGS. 38A and B, the front side of the lens optic portion is provided with a wavefront front surface portion and the back side is provided with a wavefront back surface portion.

Figure 39A:
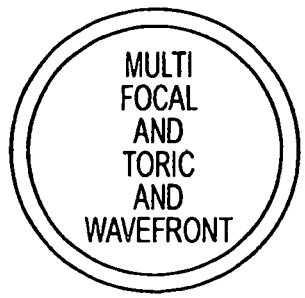
FIG. 39A is a broken away top planar view of the front side of a lens optic portion of a preferred embodiment of the accommodating artificial ocular lens (AAOL) device according to the present invention having a combined multi-focal, toric, and wavefront front surface portion.
Figure 39B:
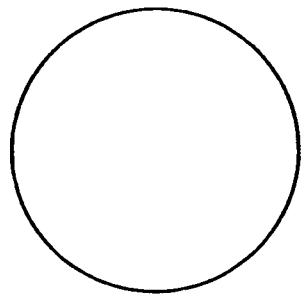
FIG. 39B is a broken away bottom planar view of the back side of the lens optic portion, as shown in FIG. 10A.

In the embodiment shown in FIGS. 39A and B, the front side of the lens optic portion is provided with combined multi-focal and toric and wavefront front surface portion and the beak side of the lens optic is provided with an optical back surface portion.

Figure 40A:
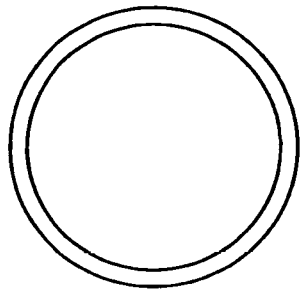
FIG. 40A is a broken away top planar view of the front side of a lens optic portion of a preferred embodiment of the accommodating artificial ocular lens (AAOL) device according to the present invention.
Figure 40B:
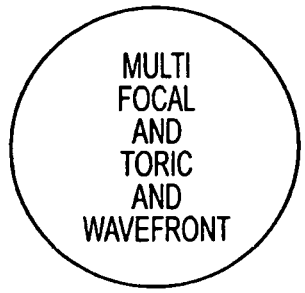
FIG. 40B is a broken away bottom planar view of the back side of the lens optic portion, as shown in FIG. 40A, having a combined multi-focal, toric, and wavefront front surface portion.

In the embodiment shown in FIGS. 40A and B, the front side of the lens optic portion is provided with an optical front surface portion and the back side of the lens optic portion is provided with a combined multi-focal and toric and wavefront surface portion.

Figure 41A:
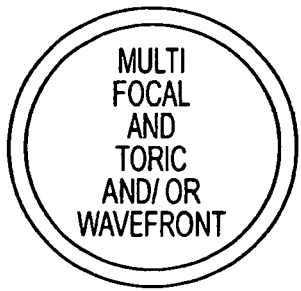
FIG. 41A is a broken away top planar view of the front side of a lens optic portion of a preferred embodiment of the accommodating artificial ocular lens (AAOL) device according to the present invention having a combined multi-focal, toric, and wavefront front surface portion.
Figure 41B:
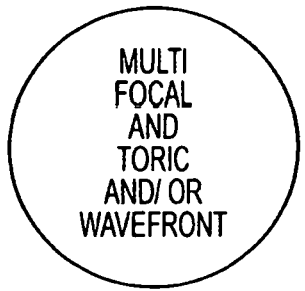
FIG. 41B is a broken away bottom planar view of the back side of the lens optic portion, as shown in FIG. 41A, having a combined multi-focal, toric, and wavefront back surface portion.

In the embodiment shown in FIGS. 41A and B, the front side of the lens optic portion is provided with at least two (2) of a multi-focal, toric and/or wavefront surface portion and the back side of the lens optic portion is provided with at least two (2) of a multi-focal, toric and wavefront surface portion.

Figure 42A:
FIG. 42A is a broken away top planar view of the front side of a lens optic portion of a preferred embodiment of the accommodating artificial ocular lens (AAOL) device according to the present invention.
Figure 42B:
FIG. 42B is a broken away bottom planar view of the back side of the lens optic portion, as shown in FIG. 42A.

In the embodiment shown in FIGS. 42A and B, the front side of the lens optic portion is provided with a multi-focal and toric and wavefront front surface portion and the back side of the lens optic portion is provided with a multi-focal and toric and wavefront back surface portion.

Figure 43A:
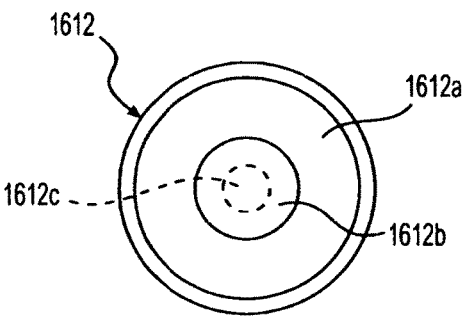
FIG. 43A is a broken away top planar view of the front side of a lens optic portion of a preferred embodiment of the accommodating artificial ocular lens (AAOL) device according to the present invention having a bifocal front surface portion.
Figure 43B:
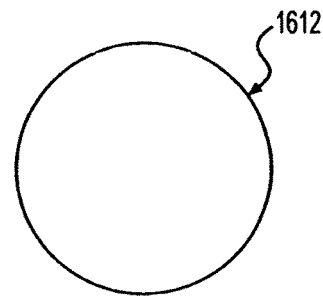
FIG. 43B is a broken away bottom planar view of the back side of the lens optic portion, as shown in FIG. 43A.

In the embodiment shown in FIGS. 43A and 43B, the front side of the lens optic portion 1612 is provided with a two (2) multi-focal and/or diffractive lens zones or surfaces 1612a, 1612b, including a circular-shaped center multi-focal and/or diffractive lens surface 1612a and a concentric outer ring-shaped multi-focal and/or diffractive lens surface 1612b on the front surface thereof. Optionally, one multi-focal and/or diffractive lens surface or zone can be provided on one (1) side of the lens optic 1612 and the other multi-focal and/or diffractive lens zone can be provide on the opposite side. As a further option, multiple multi-focal and/or diffractive lens surfaces or zones can be provided on both the front surface and back surface of the lens optic 1612. In another embodiment, the lens optic portion 1612 is provided with three (3) multi-focal and/or diffractive lens zones or surfaces 1612a, 1612b, 1612c.

For a presbyopic embodiment of the accommodating artificial ocular lens (AAOL) device 1612 according to the present invention, for example, the central additions for the lens surface 1601a should be +3.00 diopters (D). Similar but slightly different refractive correction lenses 1612 can be made for early presbyopes and late presbyopes. For example, for early presbyopes, lens surface 1612a should be +0.5 diopters (D) and for late presbyopes, lens surface 1612a should be +3.0 diopters (D). The central lens surface 1612a should be one (1) to four (4) millimeters (mm).

Again, the accommodating artificial ocular lens (AAOL) device 1612 can be provided with a third multi-focal surface or zone 1612c to provide a trifocal (e.g. −1, 0, +1). For example, three (3) object distances, the type of structure (e.g. sine wave, trapezoid and/or rectangle), and the lens material can be specified for making the trifocal embodiment. In other embodiment, more than three (3) multi-focal surfaces or zone (e.g. concentric, symmetric, asymmetric, matrix arrangements of surfaces or zones) can be used for particular applications or custom made for a particular eye. Alternatively, lithography can be used to print marks or a pattern on one or both surfaces of the lens (e.g. grid, rings, matrix) to cause light diffraction to make a diffractive lens optic, or lithography combined with etching (e.g. lens mold surface) can be used to make nanometer to angstrom dimension profiles, protrusions, patterns, contours on lens surfaces to provide multi-focal and/or defractive lens surfaces.

A variety of embodiments of the accommodating artificial ocular lens (AAOL) device having different lens haptic shapes are shown in FIGS. 44-47.

Figure 1:
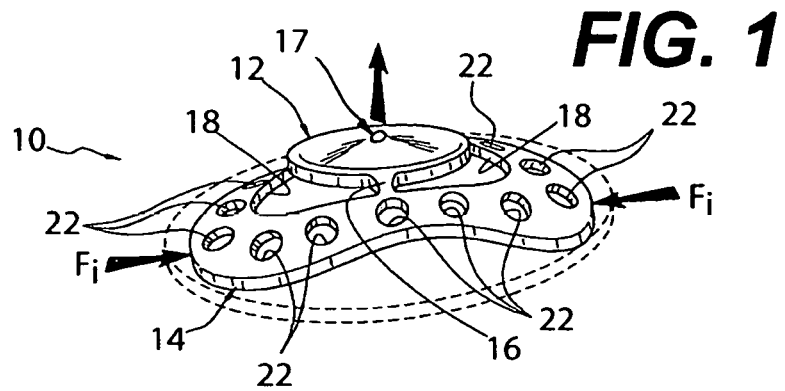
FIG. 1 is a perspective view of a deformable accommodating artificial ocular lens (AAOL) device according to the present invention shown under a stressed condition providing forward accommodation of the lens portion along the center focal axis of the eye.
Figure 44:
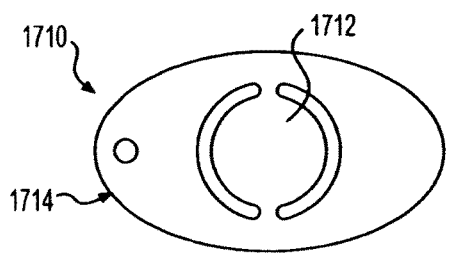
FIG. 44 is a top planar view of another embodiment of the accommodating artificial ocular lens (AAOL) device according to the present invention having an oval or ellipse shaped lens haptic portion.

In the embodiments shown in FIG. 44, the lens haptic portion 1714 is oval-shaped or spherical-shaped versus the circular-shaped configuration shown in the embodiment of FIG. 1.

Figure 45:
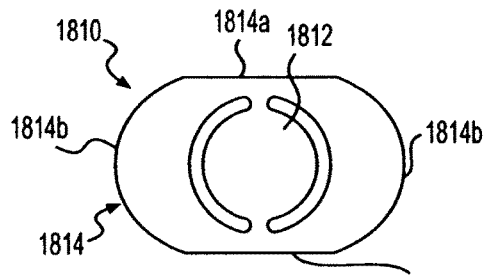
FIG. 45 is a top planar view of a further embodiment of the accommodating artificial ocular lens (AAOL) device according to the present invention having an oblong-shaped lens haptic portion.

In the embodiment shown in FIG. 45, the lens haptic portion 1814 is oblong-shaped. Specifically, the lens haptic portion 1814 has straight side portions 1814a and circular-shaped end portions 1814b.

Figure 46:
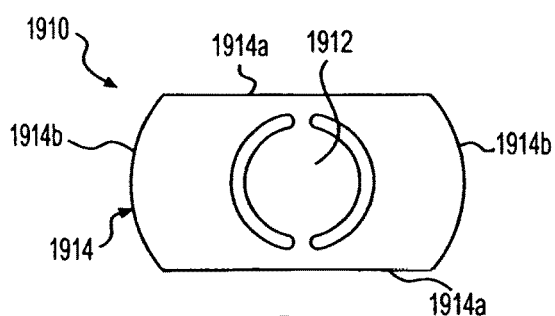
FIG. 46 is a top planar view of another further embodiment of the accommodating artificial ocular lens (AAOL) device having a rectangular-shaped lens haptic portion with round-shaped ends.

In the embodiments shown in FIG. 46, the lens haptic portion 1914 has longer straight portions 1914a (compared with the embodiment of FIG. 45) and circular-shaped end portions 1914b.

Figure 47:
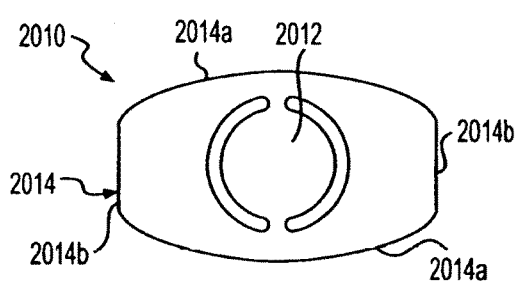
FIG. 47 is a top planar view of an even further embodiment of the accommodating artificial ocular lens (AAOL) device according to the present invention having a spheric-shaped lens haptic portion with square ends.

In the embodiments shown in FIG. 47, the lens haptic portion 2014 has oval-shaped or elliptical-shaped side portion 2014a and straight or square end portions 2014b.

Figure 48:
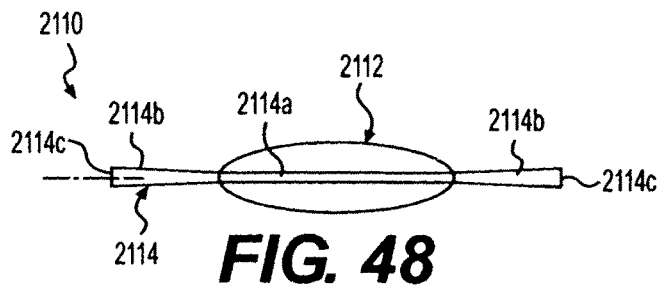
FIG. 48 is a side elevational view of another accommodating artificial ocular lens (AAOL) device having a tapering lens haptic portion.
Figure 49:
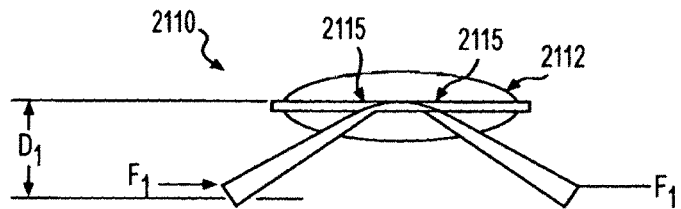
FIG. 49 is a side elevational view of the embodiment shown in FIG. 48, in a stressed and bowed condition.

In the embodiment shown in FIGS. 48 and 49, the accommodating artificial ocular lens (AAOL) device 2110 includes a tapering lens haptic portion 2114. Specifically, the thickness of the center lens haptic portion 2114a is substantially uniform and thin, and then begins to taper and thicken in an outwardly direction to define tapered lens haptic portions 2114b. The tapering and thickening of the lens haptic end portions 2114b strengthens the tapered lens haptic portions 2114b towards the lens haptic portion ends 2114a thereof to prevent bending along the length of the tapered lens haptic portions 2114b. In this manner, as shown in FIG. 49, the tapered lens haptic portions 2114b bend sharply at points 2115 (i.e. bending force is concentrated at positions 2114b). This arrangement significantly increases the accommodating or throw distance $D_1$ of the lens optic 2112 compared with an embodiment having a uniform thickness lens haptic portion.

Figure 50:
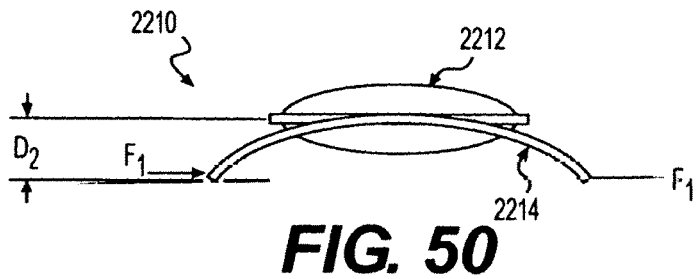
FIG. 50 is a side elevational view of a further embodiment of the accommodating artificial ocular lens (AAOL) device according to the present invention for comparing with the embodiment of FIG. 48.

To further illustrate this effect, a comparison embodiment of the accommodating artificial ocular lens (AAOL) device 2210 is shown in FIG. 50 having a uniform thickness lens haptic portion 2214. In this embodiment, the lens haptic portion 2214 bends uniformly from end-to-end (i.e. uniform curvature along length thereof) significantly reducing the accommodating or throw distance $D_2$ compared with $D_1$ of the accommodating artificial ocular lens (AAOL) device 2110. Thus, the tapering of the lens haptic portion provides for a greater accommodating or throw distance for the same amount of the force $F_1$ being exerted inwardly on the ends of the lens haptic portion.

Figure 51:
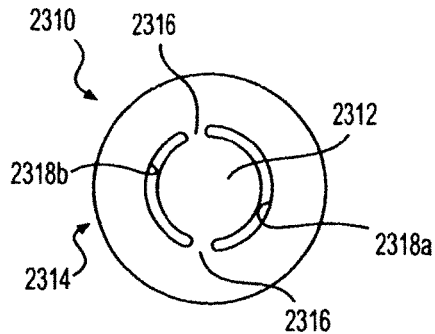
FIG. 51 is a top planar view of another further embodiment of the accommodating artificial ocular lens (AAOL) device according to the present invention.
Figure 52:
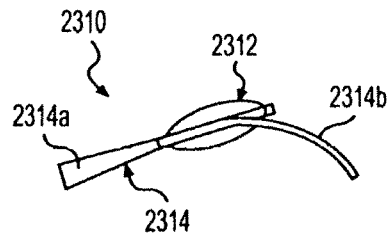
FIG. 52 is a side elevational view of the embodiment shown in FIG. 51.
Figure 57:
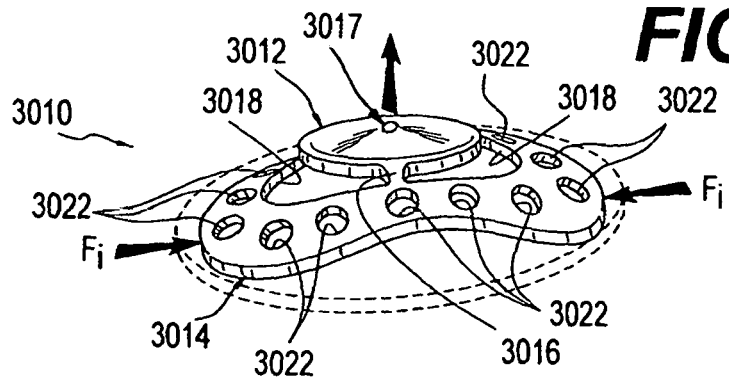
FIG. 57 is a perspective view of a deformable accommodating intraocular lens device shown under a stressed condition providing forward accommodation of the lens portion along the center focal axis of the eye.
Figure 58:
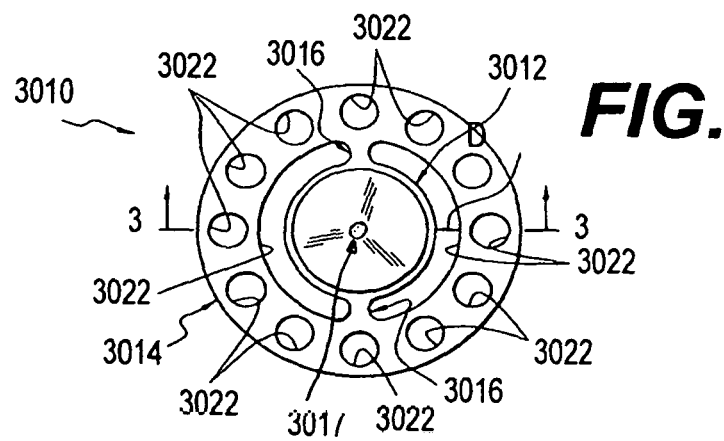
FIG. 58 is a top planar view of the deformable accommodating intraocular lens device, as shown in FIG. 1.
Figure 59:
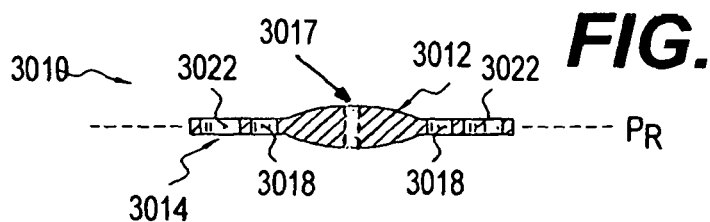
FIG. 59 is a cross-sectional view of the deformable accommodating intraocular lens device, as indicated in FIG. 2, in an unstressed condition.
Figure 60:
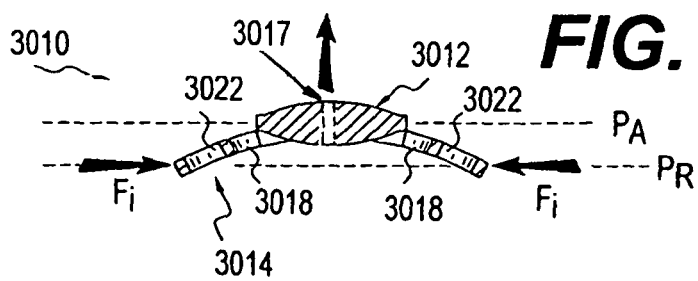
FIG. 60 is a cross-sectional view, as shown in FIG. 3, when the lens device is in a stressed condition.

In the embodiment of the accommodating artificial ocular lens (AAOL) device 2310 shown in FIGS. 51 and 52, the lens optic portion 2312 is progressively tilted as the lens haptic portion 2314 is further bowed. The tilting of the lens optic portion 2312 increases to the optical power of the lens optic portion 2312. To provide tilting of the lens optic portion 2312, the circular-shaped lens openings 2318a, 2318b are made asymmetric in size and/or shape. Further, one side of the lens haptic portion 2314 can be made thicker and/or tapered verses the other side. Specifically, the left lens haptic portion 2314a tapers in thickness outwardly from the lens optic portion 2312 while the right lens haptic portion 2314b remains uniform and thin. In this manner when inwardly force is applied to the ends of the lens haptic portion 2314, the left lens haptic portion 2314a does not bend while the right lens haptic portion 2314b significantly bends causing the lens optic 2312 to progressively bow. The lens haptic portion 2314 can be designed to provide a linear progressive tilting of the lens optic portion 2312, or an exponential progressive tilting of the lens optic portion 2312 relative to the magnitude of the inwardly force applied to the ends of the lens haptic portion 2314 (or relative to the degree of bowing of the lens haptic portion 2314).

In the embodiment shown in FIGS. 53 and 54, the accommodating artificial ocular lens (AAOL) device 2410 is configured to laterally shift the center of the lens optic portion 2412 upon application of inwardly force applied to the ends of the lens haptic portion 2414. For example, the center of the lens optic 2412 is offset from the center of the lens haptic portion 2414, as shown in FIG. 53, when the accommodating artificial ocular lens (AAOL) device 2410 is in an unstressed condition. Further, the left lens haptic portion 2414a is tapered in thickness to prevent bending while the right lens haptic portion 2414b is uniform and thin in thickness. When inwardly force is applied to the ends of the lens haptic portion 2414, the center of the lens optic 2412 shifts to the left by a distance $\Delta_C$ while the lens optic portion 2412 remains level or untilted. Alternatively, the cross-sectional size and/or shape of the connecting arms 2416 can be varied and/or the material varied to cause the same or similar effect.

An accommodating artificial ocular lens (AAOL) device can be configured to both tilt the lens optic portion and laterally shift the center of the lens optic portion in some applications by combining the features described above.

To make the custom accommodating artificial ocular lens (AAOL) device according to the present invention, the patient's eye must be carefully analyzed, measured and mapped to determine the specifications of the accommodating artificial ocular lens (AAOL) device to be manufactured. Specifically, the following is a list of specifications of the accommodating artificial ocular lens (AAOL) device to be considered and then specified, including but not limited to:

Example 1

| | |
|---|---|
| 1) refraction | Exact Diopter (D) to 0.00 D |
| 2) diffraction | |
| 3) aspheric | yes/no, any special degree |
| 4) presbyopia | yes/no |
| 5) multifocal optic | 50 cm to infinity |
|    bifocal | |
|    trifocal | |
|    accommodating IOL | 38 cm to infinity |
|    combinations | 19 cm to infinity |
|    bifocal | |

-continued

| | |
|---|---|
| trifocal | |
| 6) astigitism | |
|   how much | diaopters |
|   where located | degrees |
|   what shape | many |
| 7) Aberration | |
|   cornea | |
|   lens | |
|   retina | |
|   combined | |
|   what shape | |
|   where located | |
|   how much | |
| 8) optic | |
|   size | 2.5 to 7 mm |
|   shape | round elliptical other |
|   location | centered or decentered |
|   where | degrees |
|   concentric | yes/no |
|   symmetrical | yes/no |
| 9) overall lens size | made to fit eye or bag |
|   shape | round   8 to 15 mm |
| | elliptical  8 to 15 mm |
| | other   8 to 15 mm |
| 10) lens optic material | |
|   silicone | clear   yellow |
|   acrylic | clear   yellow |
|   soft polyimide | clear   yellow |
|   hard polyimide | clear   yellow |
|   PMMA | clear   colorless |
|   Collagen-containing polymer | clear   yellow blue light blocking additive* |
| 11) lens haptic material | |
|   silicone | |
|   acrylic | |
|   soft polyimide | |
|   collagen-containing polymer | |
| 12) transmission of date manufacturing IOL from data testing IOL from data | eye model data, topography-trace data |
| 13) any other special and/or custom features | |

*yellow is the blue light blocking mechanism

Example 2

The following is an example of a patient information request form to gather information for prescribing and specifying a custom accommodating artificial ocular lens (AAOL) device according to the present invention.
1) Dr. Name
2) Dr. Practice Name
3) address
4) phone number and email address
5) patient Name
6) patient Code
7) which Eye OS OD Both
8) AC Depth
9) axial length
10) refraction (Exact, 00D)
11) aspheric correction Yes No/Amount
12) presbyopia Yes/No
preferred reading distance
how close up? (19 cm to 50 cm)
which Lens Design
accommodating (38 CM)
multifocal (50 cm) defractive/refractive
tri-focal/bi focal
combination (19 cm to 50 cm)
trifocal/bifocal
13) astigmatism, describe:
(amount)
(location in degree)
with rule against rule oblique
other-describe
14) aberration: Best Zerneky Model
cornea/lens/retina/total
amount
location
cornea
spherical aberration
high order astigmatism
trefoil
other describe
15) other items needed
pupil concentric/non-concentric
16) lens construction
one (1) piece
two (2) piece etc.
17) material preference (lens optic portion)
silicone
acrylic
collagen-containing polymer
polyimide (soft type)
polyimide (hard type)
PMMA blue light blocking additive (yes/no)
18) material preference (lens haptic portion)
silicone
acrylic
collagen-containing polymer polyimide (soft type)
blue light blocking additive (yes/no)
19) optical size 2.5 to 7 mm
overall diameter 8 to 15 mm
20) optical symmetrical/non-symmetrical/excentric At the eye surgeon's office, the patient's eye is measured using visual field analyzers, eye charts and a topographer/abberometer. The abberometer measures the aberrations in the patient's eye and provides the eye surgeon with a topography map outlining all the aberrations. The eye surgeon uses the abberometer to check where the aberrations are coming from and analyze the data for different pathologies and make changes to the data where necessary. The abberometer is then used to generate a topography map and digital data that will be transferred to the manufacturer in the form of a customized lens order via satellite, internet, telephonic down load, CD ROM, DVD or mail or fax. Abberometer obtains the necessary information by using the Shack Hartman or means, which analyzes multiple beams of light transferred to the retina and then returned back through the eye. Variations of the light are measured against a light standard that would give perfect vision if all the parameters are met. The variation of the light is then compared against the Zerkeny polynomial to determine whether the variations are in the form of low order aberrations usually spherical and cylinder (toric) or high order aberrations such coma; trefoil (shapes showing in the optic system that look like a starburst usually around the periphery of the eye extending toward the center.

This information will then be received by the manufacturer, analyzed for completeness and any other kind of transmission errors. The data received is in the form of data points to be run through a program that to invert or reverse the information, since to correct an optic system requires making points or corrections that are opposite of the actual data received. This data will be run through the program to convert the data converted into machine language that will form a JFL file that will tell any equipment that can have varying cut (the Presitech Optiform with a variable forming tools or the DAC system with its toric generator) to cut a mold pin or optic in a form based on the information received from the eye surgeon's topography/abberometer, Zydekia Chart etc.

The order depending on the method of manufacturing can create a lens optic as part of the shop order or create a mold pin for the shop order in case of silicone manufacturing. The shop order would then go through the manufacturing process for developing lenses and a final lens optic would be made. During the process the lens would be marked in a manner so that the eye surgeon doing the surgery can tell where on the lens optic the changes are made. One side of the optic can contain all the changes needed for a multi-focal, toric and/or wavefront corrections, or some changes can be on the front side and some on the back side of the accommodating artificial ocular lens (AAOL) device depending on the patient and manufacturing constraints. In order to know that what was manufactured is what was ordered, similar equipment would be used to generate the data such as an abberometer using the same theoretical method to measure the reverse aberrations created in the lens and compare it with the original input information. The accommodating artificial ocular lens (AAOL) device is then sterilized and sent to the eye surgeon.

The manufactured lens data can be sent back with the lens to the eye surgeon, including data points and topography map with a manufacturing certificate for the eye surgeon and patient similar to a patient ID card, instead it would have a topography of the lens on the card.

The eye surgeon then inserts the lens haptic and lens optic into the patient's eye and places the accommodating artificial ocular lens (AAOL) device where needed based on what was ordered received. Minor adjustments in the lens optic and lens haptic can be made to obtain the appropriate axis of the optic. It is possible to make and optic off center in a mold pin combination if it were determined up front exactly where and if the optic needed to be changed from its center point. It is also possible to put adjustments items on the optic and haptic whereby the optic could be shifted up, down or side ways so that the multi-focal, toric, wave front can be lined up to give the patient better vision.

Lens Operation

The accommodating artificial ocular lens (AAOL) device according to the present invention is configured to bow or flex due to forces applied by the eye to the accommodating artificial ocular lens (AAOL) device, in particular to forces applied to the edge portions of the lens plate haptic portion.

The accommodating artificial ocular lens (AAOL) device according to the present invention can be located potentially in the anterior chamber and/or posterior chamber of the eye. Preferably the accommodating artificial ocular lens (AAOL) device according to the present invention in located in the posterior chamber of they eye, and more preferably is located in the capsular bag of the eye after cataract lens removal.

In operation, forces that are exerted on the capsular bag by the zonules of the eye are applied to the accommodating artificial ocular lens (AAOL) device according to the present invention, in particular to the peripheral edges thereof. As forces are applied to the outer edges of the accommodating artificial ocular lens (AAOL) device according to the present invention by the eye, the lens plate haptic portion begins to bow in an arch generally perpendicular to the flexible or resilient lens arm portions connecting the lens optic portion to the lens plate haptic portion so as to move the lens optic portion either forward or rearward from a resting position depending on the particular configuration and arrangement. In any event, the accommodating artificial ocular lens (AAOL) device according to the present invention is configured so that the lens plate haptic portion moves the lens optic portion during operation.

The operation or functioning of the accommodating artificial ocular lens (AAOL) device 10 according to the present invention is shown in FIGS. 23-26.

The accommodating artificial ocular lens (AAOL) device 10 is shown in an unstressed and unbowed condition, as shown in FIGS. 23 and 24. When inwardly directed forces F; are applied around the perimeter of the plate haptic portion 14, the plate haptic portion 14 begins to bow relative to the X axis as illustrated in FIG. 25, and may furthermore be enhanced by varying hydraulic pressures in the eye. In this manner, the lens portion 12 is moved from a resting position plane P.sub.R to an accommodating plane $P_A$ and traverses a distance .DELTA.sub.A. However, as illustrated in FIG. 26, the plate haptic portion 14 does not bow or substantially bow along the transverse axis Y, since the flexible or resilient lens arm portions 16, 16 reinforce and stiffen the lens plate haptic portion 14 from bowing along this tranverse axis Y. Thus, the accommodating artificial ocular lens (AAOL) device 10 essentially bows in only a single dimension, and not in two (2) dimensions.

As illustrated in FIG. 25, the outer edges of the lens optic portion 12 become somewhat separated and exposed from the upper surface of the lens plate haptic portion 14 due to bowing of the lens plate haptic portion 14. In this manner, it is possible that the lens optic portion 12 could potentially extend into or through the pupil of the iris of the eye. However, as illustrated in FIG. 26, the lens arm portions 16, 16 do not allow the lens plate haptic portion 14 to bow in the transverse axis Y, and prevents the lens optic portion 12 from being exposed and separating from the upper surface of the plate haptic portion 14. Further, the arm portion 16 acts or functions like a pair of bumpers against the back of the iris at the opening of the pupil to prevent the lens optic portion 12 from entering into or passing through the pupil of the iris of the eye.

As illustrated in FIGS. 55 and 56, the lens optic portion 2512 remains flat in the X-Y plane even when the lens haptic portion 2514 is significantly bowed or bent due to the highly flexible nature of the connecting arms 2516. Further, the lens haptic portion 2514 can be provided with one or more marks 2515 (e.g. ink or indent) to facilitate placement and alignment when implant into the eye.

While this invention has been described with respect to various specific examples and embodiments, it is to be understood that the invention is not limited thereto and that it can be variously practiced within the scope of the following claims.

Lens Optic Window

A deformable accommodating intraocular lens device 10 is shown in FIGS. 57 to 60. This embodiment provides both dynamic accommodation and static accommodation of the vision of the eye.

The deformable accommodating intraocular lens device 3010 comprises or consists of a lens optic portion 3012 and a plate lens haptic portion 3014. The lens optic portion 3012 is connected to the plate lens haptic portion 3014 by a pair of flexible or resilient arm portions 3016, 3016, as shown in FIG. 2. The lens optic portion 3012 is provided with a lens optic window 3017.

A pair of partial circular-shaped openings 3018, 3018 separate the lens optic portion 3012 from the plate lens haptic portion 3014, as shown in FIG. 2, by a predetermined distance D. In this manner, the lens optic portion 3012 is structurally substantially independent of plate lens haptic portion 18, except at the two (2) points of connection provided by the resilient or flexible arm portion 3016, 3016.

The perimeter of the plate lens haptic portion 3014 is provided with a plurality of through holes 3022 to facilitate adherence of tissue looped through the through holes 3022 by tissue located on either side of the perimeter of the plate lens haptic portion 3014 connecting together in the through holes 3022. In this manner, once the deformable accommodating intraocular lens device 3010 has been implanted and the eye has healed, the perimeter of the plate lens haptic portion 3014 becomes substantially anchored in place.

In the embodiments shown in FIGS. 57 to 60, the lens portion 3014, plate lens haptic portion 3014, and arm portions 3016, 3016 are made as a one-piece unitary structure from soft, deformable or resilient polymer material. The deformable accommodating intraocular lens device 3010 can be inserted through a small incision (e.g. less than 2.5 millimeters) through the cornea of the eye in a deformed rolled, folded or otherwise compressed condition by use of forceps or a lens injecting device.

Figure 61:
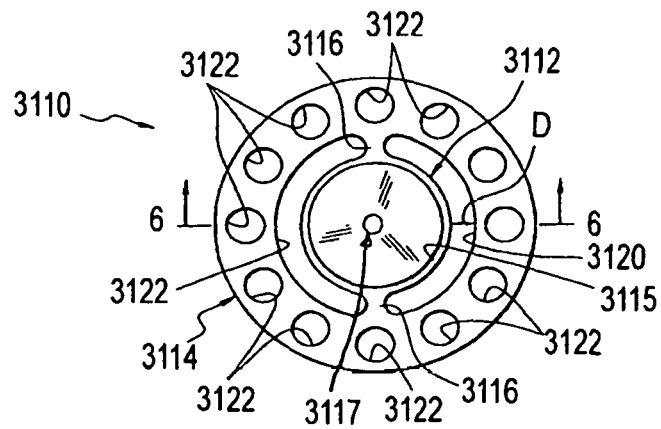
FIG. 61 is a top planar view of another embodiment of the accommodating intraocular lens device.
Figure 62:
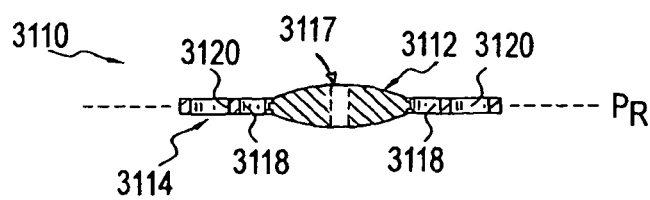
FIG. 62 is a cross-sectional view of the accommodating intraocular lens device as indicated in FIG. 5.
Figure 63:
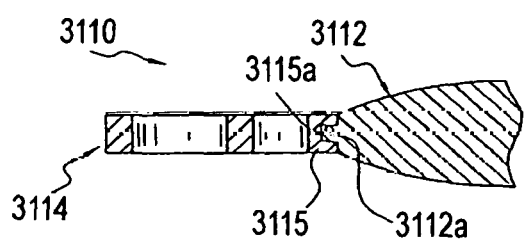
FIG. 63 is a partial broken away detailed cross-sectional view of a portion of the accommodating intraocular lens device shown in FIGS. 5 and 6.

Another embodiment of a partially deformable accommodating intraocular lens 3110 device is shown in FIGS. 61-63.

The partially deformable accommodating intraocular lens device 3110 comprises or consists of a lens optic portion 3112 and a plate lens haptic portion 3114. The lens optic portion 3112 is connected to the plate lens haptic portion 3114 by a pair of resilient or flexible arm portions 3116. The lens optic portion 3112 is provided with a lens optic window 3117.

In this embodiment, the lens optic portion 3112 is made out of non-resilient or non-deformable material such as polymethyl methacrylate. However, the plate lens haptic portion 3114 is made from a resilient polymer material and the partially deformable accommodating intraocular lens 3110 is made from two (2) separate pieces and assembled together to become a single piece lens. Further, the deformable accommodating lens can be made of a material that varies in hardness or stiffness along its length (e.g. harder lens portion and softer plate haptic portions or reverse).

The plate lens haptic portion 3114 includes a resilient lens optic carrier or lens optic receiving portion 3115 provided with an inner groove 3115*a* cooperating with a tongue portion 3112*a* of the lens optic portions 3112 as shown in FIG. 63. The lens optic portion 3112 can be secured in place due to the resilient nature of the lens optic receiver or lens optic carrier 3115 of the plate lens haptic portion 3114 due to its capacity to withstand a certain amount of band stress.

Alternatively, or in addition, the tongue portion 3112*a* can be adhered by glue, adhesive, welding or other technique to secure the lens optic portion 3112 to the lens optic receiver or lens optic carrier 3115 of the plate lens haptic portion 3114.

The partially deformable accommodating intraocular lens device is inserted through a relatively large incision in the cornea by forceps and then implanted into the capsular bag after cataract lens removal.

Figure 64:
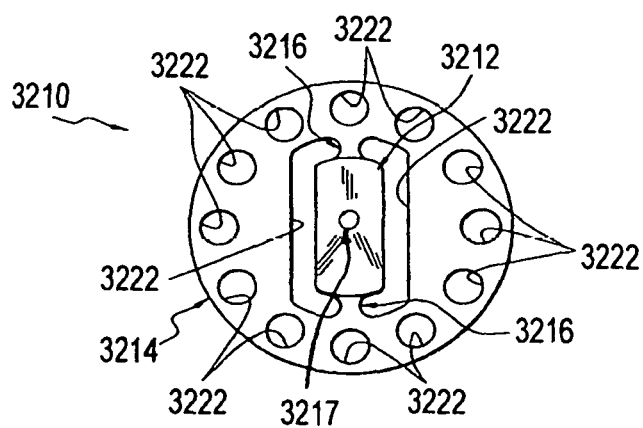
FIG. 64 is a top planar view of another embodiment of an accommodating intraocular lens.

A further embodiment of the accommodating intraocular lens 3210 is shown in FIG. 64.

The accommodating intraocular lens 3210 comprises or consists of a substantially rectangular lens optic portion 3212 connected to a round-shaped plate lens haptic portion 3214 by a pair of flexible or resilient arm portions 3216, 3216. The lens optic portion 3212 is provided with a lens optic window 3217.

A pair of oblong or partial oval-shaped openings 3220, 3220 are provided between the lens optic portion 3212 and the plate lens haptic portion 3214. A plurality of through holes 3222 are provided to facilitate anchoring of the perimeter of the plate lens haptic portion 3214.

Figure 65:
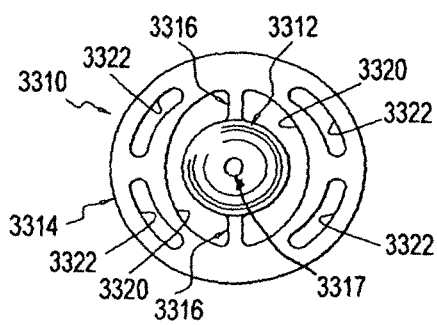
FIG. 65 is a top planar view of another embodiment of the accommodating intraocular lens.

A further embodiment of the accommodating intraocular lens 3310 is shown in FIG. 65.

The accommodating intraocular lens 3310 comprises or consists of a substantially round lens optic portion 3312 connected to a round plate lens haptic portion 3314 by a pair of flexible or resilient arm portions 3316, 3316. The lens optic portion 3312 is provided with a lens optic window 3317.

A pair of oblong or partial oval-shaped openings 3320, 3320 are provided between the lens optic portion 3312 and the plate lens haptic portion 3314. A plurality of through holes 3322 are provided to facilitate anchoring of the perimeter of the plate lens haptic portion 3314.

Figure 66:
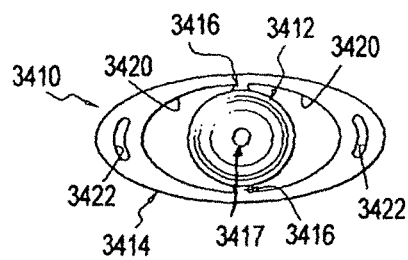
FIG. 66 is a top planar view of another embodiment of the accommodating intraocular lens.

A further embodiment of the accommodating intraocular lens 3410 is shown in FIG. 66.

The accommodating intraocular lens 3410 comprises or consists of a substantially round lens optic portion 3412 connected to an oblong-shape plate lens haptic portion 3414 by a pair of flexible or resilient arm portions 3416, 3416. The lens optic portion 3412 is provided with a lens optic window 3417.

A pair of oblong or partial oval-shaped openings 3420, 3420 are provided between the lens optic portion 3412 and the plate lens haptic portion 3414. A plurality of through holes 3422 are provided to facilitate anchoring of the perimeter of the plate lens haptic portion 3414.

Figure 67:
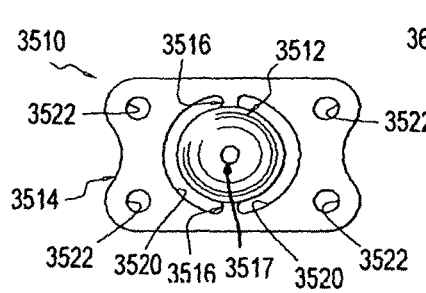
FIG. 67 is a top planar view of another embodiment of the accommodating intraocular lens.

A further embodiment of the accommodating intraocular lens 3510 is shown in FIG. 67.

The accommodating intraocular lens 3510 comprises or consists of a round lens optic portion 3512 connected to a modified oblong-shape plate lens haptic portion 3514 by a pair of flexible or resilient arm portions 3516, 3516. The lens optic portion 3512 is provided with a lens optic window 3517.

A pair of oblong or partial oval-shaped openings 3520, 3520 are provided between the lens optic portion 3512 and the plate lens haptic portion 3514. A plurality of through holes 3522 are provided to facilitate anchoring of the perimeter of the plate lens haptic portion 3514.

Figure 68:
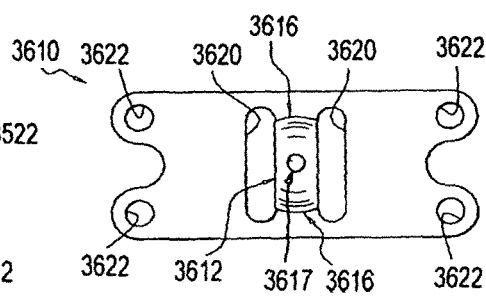
FIG. 68 is a top planar view of another embodiment of the accommodating intraocular lens.

Another embodiment of the accommodating intraocular lens 3610 is shown in FIG. 68.

The accommodating intraocular lens 3610 comprises or consists of an elongated lens optic portion 3612 connected to an elongated plate lens haptic portion 3614 by a pair of flexible or resilient arm portions 3616, 3616. The lens optic portion 3612 is provided with a lens optic window 3617.

A pair of oblong-shaped openings 3620, 3620 are provided between the lens optic portion 3612 and the plate lens haptic portion 3614. A plurality of through holes 3622 are provided to facilitate anchoring of the ends of the plate lens haptic portion 3614 in the eye.

Figure 69:
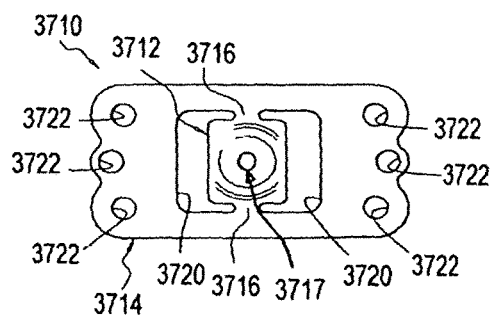
FIG. 69 is a top planar view of another embodiment of an accommodating intraocular lens.

A further embodiment of the accommodating intraocular lens 3710 is shown in FIG. 69. The accommodating intraocular lens 3710 comprises or consists of a rectangular lens optic portion 3712 connected to a rectangular plate lens haptic portion 3714 by a pair of flexible or resilient arm portions 3716, 3716. The lens optic portion 3712 is provided with a lens optic window 3717.

A pair of rectangular oval-shaped openings 3720, 3720 are provided between the lens optic portion 3712 and the plate lens haptic portion 3714. A plurality of through holes 3722 are provided to facilitate anchoring of the ends of the plate lens haptic portion 3714 in the eye.

Figure 70:
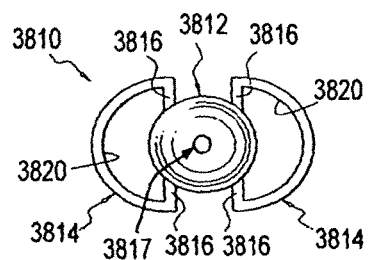
FIG. 70 is a top planar view of another embodiment of the accommodating intraocular lens.

An even further embodiment of the accommodating intraocular lens 3810 is shown in FIG. 70.

The accommodating intraocular lens 3810 comprises or consists of a round lens optic portion 3812 connected to a pair of half-circle plate lens haptic portions 3814, 3814 each by a pair of flexible or resilient arm portions 3816, 816. The lens optic portion 3812 is provided with a lens optic window 3817.

A pair of half-circle shaped openings 3820, 3820 are provided between the lens optic portion 3812 and the plate lens haptic portions 3814, 3814. In this embodiment, the openings 3820, 3820 also provide the function of through holes in previous embodiments to facilitate anchoring the ends of the plate lens haptic portions 3814, 3814 in the eye.

Figure 71:
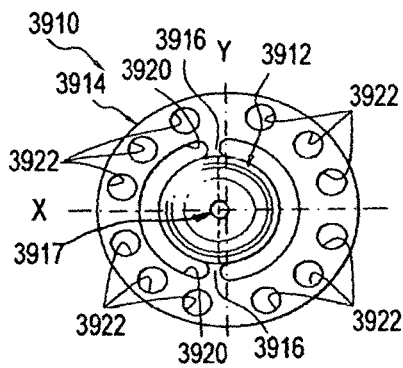
FIG. 71 is a top planar view of a further embodiment of the accommodating intraocular lens.

Another embodiment of the accommodating intraocular lens 3910 is shown FIG. 71.

The accommodating intraocular lens 3910 comprises or consists of a round lens optic portion 3912 connected to a round plate lens haptic portion 3914 by a pair of flexible or resilient arm portions 3916, 3916. The arm portions 3916, 3916 are approximately the same length. The lens optic portion 3912 is provided with a lens optic window 3917.

A pair of half circular-shaped openings 3920, 3920 are provided between the lens optic portion 3912 and the plate lens haptic portion 3914. A plurality of through holes 3922 are provided to facilitate anchoring the plate lens haptic portion 3914 in the eye. In this embodiment, the lens optic portion 3912 is located off centered along the Y axis making the round plate lens haptic portion somewhat asymmetrical in shape relative to the X axis.

Figure 72:
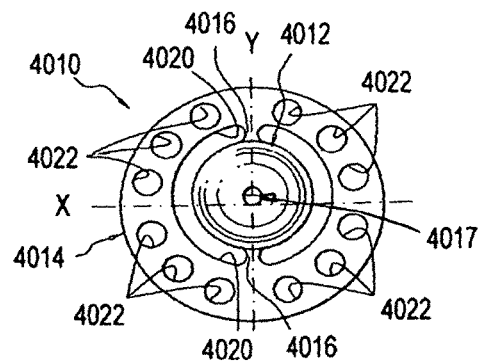
FIG. 72 is a top planar view of a further embodiment of the accommodating intraocular lens.

Another embodiment of the accommodating intraocular lens 4010 is shown in FIG. 72.

The accommodating intraocular lens 4010 comprises or consists of a round lens optic portion 4012 connected to a round plate lens haptic portion 4014 by a pair of flexible or resilient arm portions 4016, 4016. The lens optic portion 4012 is provided with a lens optic window 4017.

A pair of half circle-shaped openings 4020, 4020 are provided between the lens optic portion 4012 and the plate lens haptic portion 4014. A plurality of through holes 4022 are provided to facilitate anchoring the perimeter of the plate lens haptic portion 4014 in the eye. In this embodiment, the lens portion 4012 is located off center along the X axis resulting in the plate lens haptic portion 4014 being asymmetrical relative to the Y axis.

Figure 73:
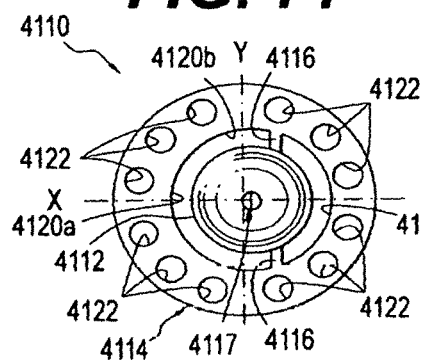
FIG. 73 is a top planar view of a further embodiment of the accommodating intraocular lens.

Another embodiment of the accommodating intraocular lens 4110 is shown in FIG. 73.

The accommodating intraocular lens 4110 comprises or consists of a round lens optic portion 4112 connected to a round plate lens haptic portion 4114 by a pair of flexible or resilient arm portions 4116, 4116. The arm portions 4116, 4116 are both located off axis relative to the Y axis. The lens optic portion 4112 is provided with a lens optic window 4117.

A pair of half circular-shaped openings 4120a, 4120b are provided between the lens optic portion 4112 and the plate lens haptic portion 4114. It is to be noted that the opening 4120a is larger than the opening 4120b. A plurality of through holes 4122 are provided to facilitate anchoring of the perimeter of the plate lens haptic portion 4114 in the eye.

Figure 74:
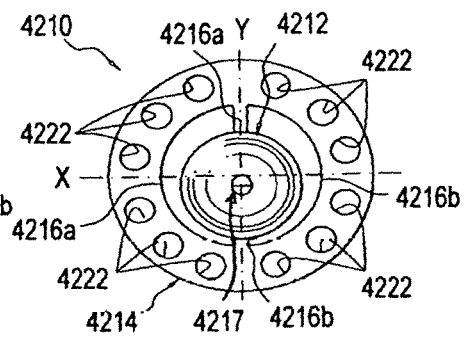
FIG. 74 is a top planar view of a further embodiment of the accommodating intraocular lens.

Another embodiment of the accommodating intraocular lens 4210 is shown in FIG. 74.

The accommodating intraocular lens 4210 comprises or consists of a round lens optic portion 4212 connected to a round plate lens haptic portion 4214 by a pair of flexible or resilient arm portions 4216a and 4216b. It is to be noted that the arm portion 4216a is longer than the arm portion 4216b. The lens optic portion 4212 is provided with a lens optic window 4217.

A pair of asymmetrical half circular-shaped openings 4220 are provided between the lens optic portion 4212 and the plate lens haptic portion 4214. A plurality of through holes 4222 are provided to facilitate anchoring of the perimeter of the plate lens haptic portion 4214 in the eye.

Figure 75:
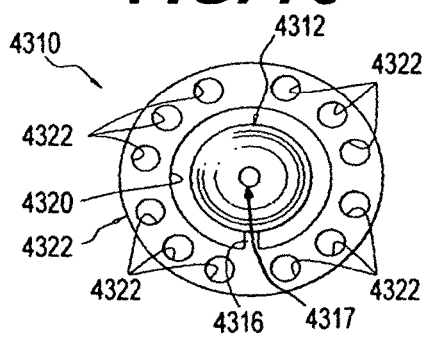
FIG. 75 is a top planar view of a further embodiment of the accommodating intraocular lens.

Another embodiment of the accommodating intraocular lens 4310 is shown in FIG. 75.

The accommodating intraocular lens 4310 comprises or consists of a round lens optic portion 4312 connected to a round plate lens haptic portion 4314 by a single flexible or resilient arm portion 4316. The lens optic portion 4312 is provided with a lens optic window 4317.

A single circular-shaped opening 4320 is provided to separate the lens optic portion 4312 from the plate lens haptic portion 4314. A plurality of through holes 4322 are provided to facilitate anchoring of the perimeter of the plate lens haptic portion 4314 in the eye.

Figure 76:
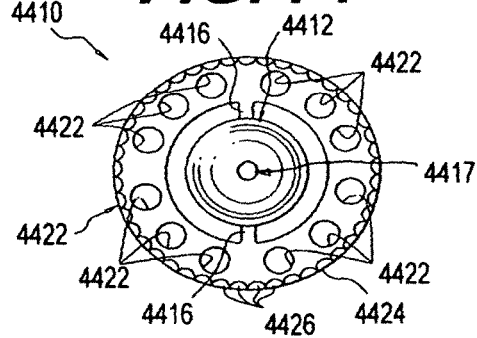
FIG. 76 is a top planar view of a further embodiment of the accommodating intraocular lens.

Another embodiment of the accommodating intraocular lens 4410 is shown in FIG. 76.

The accommodating intraocular lens 4410 comprises or consists of a round lens optic portion 4412 connected to a round plate lens haptic portion 4414 by a pair of flexible or resilient arm portions 4416, 4416. The lens optic portion 4412 is provided with a lens optic window 4417.

A pair of half circular-shaped openings 4420, 41420 are provided between the lens optic portion 4412 and the plate lens haptic portion 4414. A plurality of through holes 4422 are provided to facilitate anchoring of the perimeter of the plate lens haptic portion 4414 in the eye. In addition, the edge 4424 is provided with scalloped portions 4426 around the perimeter thereof to facilitate the fibrotic fixation process. Alternatively, or in addition, the scallops can be replaced with a roughened surface, porous surface, serrations, notches and/or flaps.

A double lens embodiment of the accommodating intraocular lens 4510 is shown in FIGS. 77 and 78.

The accommodating lens 4510 comprises or consists of a front accommodating lens optic portion 4510a and a back accommodating lens optic portion 4510b. The lens optic portion 4510a and the lens optic portion 4510b are essentially the same configuration except reverse oriented and assembled back-to-back.

The accommodating intraocular lens portion 4510a includes a round lens optic portion 4512a connected to a round plate lens haptic portion 4514a by a pair of flexible or resilient arm portions 4516a, 4516a. The lens optic portions 4512a is provided with a lens optic window 4517a.

A pair of half circular-shaped openings 4520a, 4520a are provided between the lens optic portion 4512a and the plate lens haptic portion 4514a. A plurality of through holes 4522a are provided to facilitate anchoring of the perimeter of the plate lens haptic portion 4514a in the eye.

The accommodating lens portion 4510b is the same or similarly configured to the accommodating lens portion 4510a. The lens optic portion 4512b is provided with a lens optic window 4517b.

As shown in FIG. 78, the outer edges or perimeter of the lens portions 4510a and 4510b contact, engage, or connected to each other when implanted in the eye.

An example of an accommodating intraocular lens haptic portion can have a length preferably from 8 millimeters to 13 millimeters, a width from 5 to 13 millimeters, and a thickness from 0.05 millimeters to 1 millimeter. The opening distance D is preferably 0.20 to 3.0 millimeters. It is important that the ratio of the radial length of the plate lens haptic portion relative to the axial thickness of the plate lens haptic portion is preferably 1.5 to 8 or more, to provide sufficient bowing of the plate lens haptic portion when stressed inwardly by forces applied by the eye.

An example of a deformable accommodating intraocular lens device 4610 is shown in FIGS. 83-85.

The deformable accommodating intraocular lens 4610 comprises or consists of a lens optic portion 4612, a plate lens haptic portion 4614, and a lens optical window 4617. In this embodiment, the lens optical window 4617 is configured as a flat lens optic portion 4619 provided on at least one side of the lens optic portion 4612. Alternatively, the flat lens optic portion 4619 can be located off-center (e.g. slightly off-center).

The flat lens optic portion 4619 is a portion of the lens optic portion 4612 having slight curvature or no curvature relative to the surrounding lens optic portion 4612. Preferably, the flat lens optic portion 4619 is made as flat as possible to maximize light transmittance perpendicular to the lens plane therethrough. Further, the transition between the flat lens optic portion 4619 and surrounding lens optic portion 4612 can be smoothed to avoid a discontinuous transition (e.g. curve smoothing shape).

In the example shown in FIGS. 83-85, the flat lens optic portions 4619, 4619 are provided on both sides of the lens optic portion 4612. It is noted that the one flat lens optic portion 4619 overlaps the other flat lens optic portion 4619. Alternatively, the flat lens portions can be configured to partially overlap, or not overlap.

Further, it is noted that the one flat lens optic portion 4619 is the same shape (e.g. circle or circular) and the same size (e.g. 1 mm) as the other flat lens portion 4619. Alternatively, the flat lens portion can have a different shape (e.g. oval, triangle, square, rectangle, pentagon, hexagon, octagon, star-shaped, gear-shaped), and/or can have a different size (e.g. overlapping larger circle on one side of lens and small circle on opposite side).

The lens plate haptic portion 4614 is provide with two through holes 4621 to allow anchoring of the accommodating intraocular lens 4610 within the eye.

An example of a deformable accommodating intraocular lens device 4710 is shown in FIGS. 86 and 87.

The deformable accommodating intraocular lens 4710 comprises or consists of a lens optic portion 4712, a plate lens haptic portion 4714, and a lens optical window 4717. In this embodiment, the lens optical window 4717 is configured as a flat lens optic portion 4719 provided on at least one side of the lens optic portion 4712. Alternatively, the flat lens optic portion 4719 can be located off-center (e.g. slightly off-center).

The flat lens optic portions 4717, 4717 are slightly raised above the curved front and back surfaces of the lens optic portion 4712.

An example of a deformable accommodating intraocular lens device 4810 is shown in FIGS. 88 and 89.

The deformable accommodating intraocular lens 4810 comprises or consists of a lens optic portion 4812, a plate lens haptic portion 4814, and a lens optic window 4817. In this embodiment, the lens optic window 4817 is configured as a lens optic hole 4819 (e.g. through hole or partial hole or holes) provided on at least one side of the lens optic portion 4812.

The lens optic hole 4819 is located in the lens optic portion 4812. The lens optic hole 4819 is preferably configured to maximize light transmittance perpendicular to the lens plane through the lens optic portion 4812. Further, the transition between the lens optic hole 4819 and surrounding lens optic portion 4812 can be smoothed to avoid a discontinuous transition (e.g. curve smoothing shape).

A preferred embodiment of a deformable accommodating intraocular lens device 4910 is shown in FIGS. 90 and 91. The deformable accommodating intraocular lens 4910 provides for static accommodation of vision of the eye.

The deformable accommodating intraocular lens 4910 comprises or consists of a lens optic portion 4912, a plate lens haptic portion 4914, and a lens optic window 4917. In this embodiment, the lens optical window 4917 is configured as a tapering lens optic hole 4919 (e.g. through hole or partial hole or holes) provided on at least one side of the lens optic portion 4912.

The lens optical hole 4919 is located in the lens optic portion 4912. The lens optic hole 4919 is preferably configured to maximize light transmittance perpendicular to the lens plane through the lens optic portion 4912. Further, the transition between the lens optic hole 4919 and surrounding lens optic portion 4912 can be smoothed to avoid a discontinuous transition (e.g. curve smoothing shape).

A plurality of embodiments of the accommodating lens device comprising or consisting of a lens optic configured with a lens optic window, is shown in FIGS. 92-99. The lens device embodiments are shown without a haptic or haptics; however, the lens device embodiment can including a haptic or haptics.

Figures 92, 93, 94, 95:
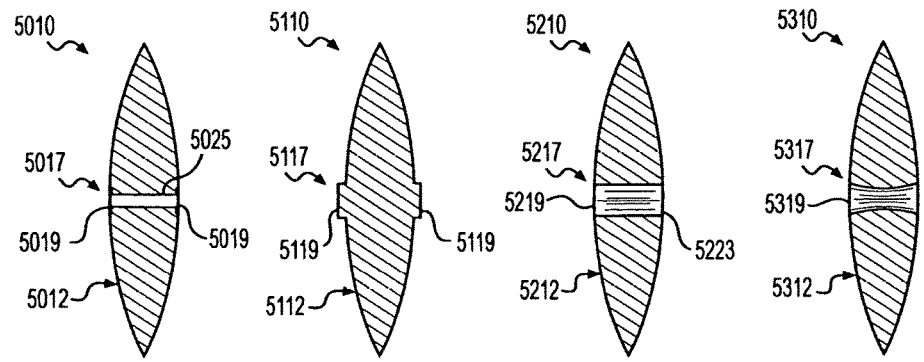
FIG. 92 is a center cross-sectional view of an accommodating intraocular lens comprising or consisting of a lens optic window comprising a flat lens optic portion and a lens optic hole provided in the lens optic portion.
FIG. 93 is a center cross-sectional view of an accommodating intraocular lens comprising or consisting of a lens optic window comprising a raised flat lens optic portion provided in the lens optic portion.
FIG. 94 is a center cross-sectional view of an accommodating intraocular lens comprising or consisting of a lens optic window comprising a lens optic hole provided in the lens optic portion.
FIG. 95 is a center cross-sectional view of an accommodating intraocular lens comprising or consisting of a lens optic window comprising a tapering lens optic hole provided in the lens optic portion.

An accommodating intraocular lens 5010 comprising of or consisting of a lens optic 5012 is shown in FIG. 92. The lens optic 5012 comprises a lens optic window 5017 configured as at least one flat lens optic portion 5019.

An accommodating intraocular lens 5110 comprising or consisting of a lens optic 5112 is shown in FIG. 93. The lens optic 5112 comprises a lens optic window 5117 configured as at least one raised flat lens optic portion 5119.

An accommodating intraocular lens 5210 comprising or consisting of a lens optic 5212 is shown in FIG. 94. The lens optic 5212 comprises a lens optic window 5217 configured as a lens optic tunnel 5219. The lens optic tunnel is provided with a light barrier 5223 (e.g. frosted surface or insert, opaque surface or insert, colored surface or insert, reflecting surface or insert) to prevent light from the lens optic 5212 from entering the lens optic tunnel 5219.

An accommodating intraocular lens 5310 comprising of or consisting of a lens optic 5312 shown in FIG. 95. The lens optic 5312 comprises a lens optic window 5317 configured as a tapering lens optic hole 5319 tapering outwardly from a center of the lens 5310.

Figures 96, 97, 98, 99:
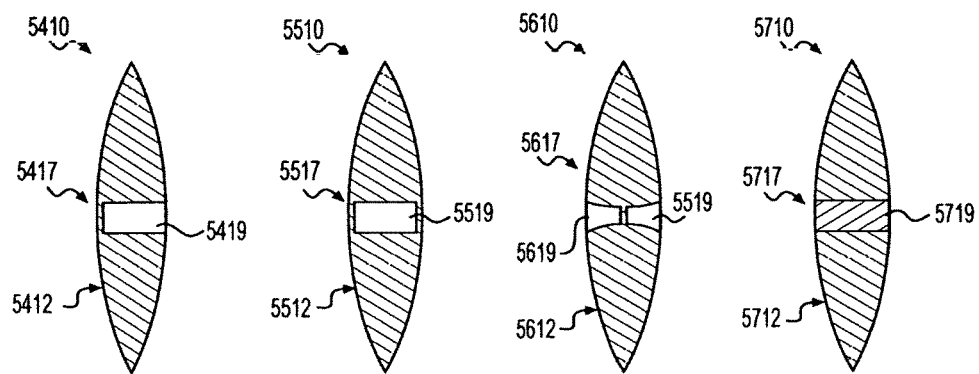
FIG. 96 is a center cross-sectional view of an accommodating intraocular lens comprising or consisting of a lens optic window comprising a partial lens optic hole provided in the lens optic portion.
FIG. 97 is a center cross-sectional view of an accommodating intraocular lens comprising or consisting of a lens optic window comprising a closed sided lens optic hole or cavity provided in the lens optic portion.
FIG. 98 is a center cross-sectional view of an accommodating intraocular lens comprising or consisting of a lens optic window comprising a pair of partial tapering holes provided in the lens optic portion.
FIG. 99 is a center cross-sectional view of an accommodating intraocular lens comprising or consisting of a lens optic window comprising a fiber optic lens optic insert provided in the lens optic portion.

An accommodating intraocular lens 5410 comprising of or consisting of a lens optic 5412 shown in FIG. 96. The lens optic 5412 comprises a lens optic window 5417 configured as a partial depth lens optic hole 5419.

An accommodating intraocular lens 5510 comprising of or consisting of a lens optic 5512 shown in FIG. 97. The lens optic 5512 comprises a lens optic window 5517 configured as a closed ended lens optic hole or cavity 5519.

An accommodating intraocular lens 5610 comprising of or consisting of a lens optic 5612 shown in FIG. 98. The lens optic 5612 comprises a lens optic window 5617 configured as a pair of outwardly tapering lens optic holes 5619.

An accommodating intraocular lens 5710 comprising of or consisting of a lens optic 5712 is shown in FIG. 99. The lens optic 5712 comprises a lens optic window 5717 configured as a lens optic insert 5719 (e.g. material having different refractive index, fiber optic, fiber optic bundle, light guide).

Figure 100:
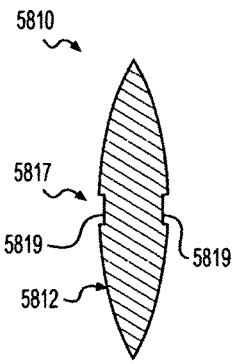
FIG. 100 is a center cross-sectional view of an accommodating intraocular lens comprising or consisting of a lens optic window comprising a partial hole or recess provided in the lens optic portion.

An accommodating intraocular lens 5810 comprising of or consisting of a lens optic 5812 is shown in FIG. 100. The lens optic 5812 comprises a lens optic window 5817 configured as a pair of partial holes or recesses 5819.

Figure 101:
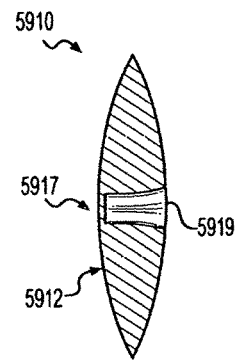
FIG. 101 is a center cross-sectional view of an accommodating intraocular lens comprising or consisting of a lens optic window comprising a partial outwardly tapering hole provided in the lens optic portion.

An accommodating intraocular lens 5910 comprising of or consisting of a lens optic 5912 is shown in FIG. 101. The lens optic 5912 comprises a lens optic window 5917 configured as an outwardly tapering hole 5919.

Figure 102:
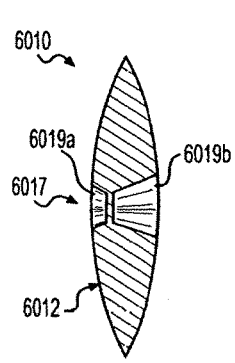
FIG. 102 is a center cross-sectional view of an accommodating intraocular lens comprising or consisting of a lens optic window comprising a pair of partial outwardly tapering holes provided in the lens optic portion.

An accommodating intraocular lens 6010 comprising of or consisting of a lens optic 6012 is shown in FIG. 102. The lens optic 6012 comprises a lens optic window 6017 configured as a pair of outwardly tapering partial holes or recesses 6019a, 6019b.

Figure 103:
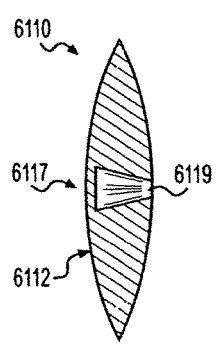

An accommodating intraocular lens 6110 comprising of or consisting of a lens optic 6112 is shown in FIG. 103. The lens optic 6112 comprises a lens optic window 6117 configured as an inwardly taping hole 6119.

Figure 104:
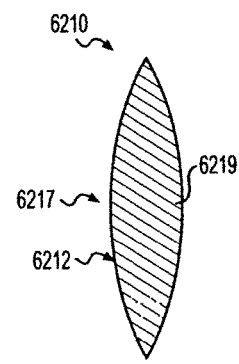

An accommodating intraocular lens 6210 comprising of or consisting of a lens optic 6212 is shown in FIG. 104. The lens optic 6212 comprises a lens optic window 6217 configured as an elliptical-shaped lens optic insert 6219.

Figure 105:
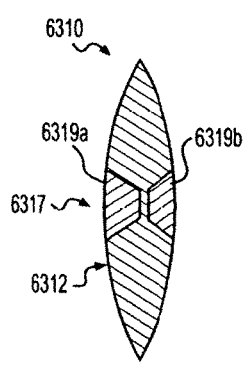

An accommodating intraocular lens 6310 comprising of or consisting of a lens optic 6312 is shown in FIG. 105. The lens optic 6312 comprises or consists of a lens optic window 6317 configured as a pair of outwardly tapering lens optic inserts 6319a, 6319b.

Figure 106:
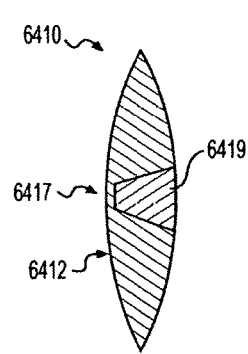

An accommodating intraocular lens 6410 comprising or consisting of a lens optic 6412 is shown in FIG. 106. The lens optic 6412 comprises a lens optic window 6417 configured as an outwardly tapering lens optic insert 6019.

Figure 107:
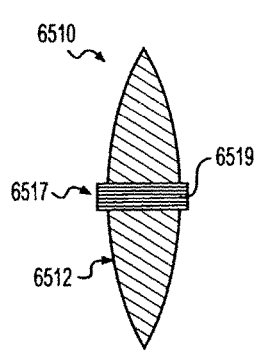

An accommodating intraocular lens 6510 comprising of or consisting of a lens optic 6512 is shown in FIG. 107. The lens optic 6512 comprises a lens optic window 6517 configured as lens optic insert 6519 having outwardly extending ends (e.g. fiber optic bundle, light guide).

Figure 108:
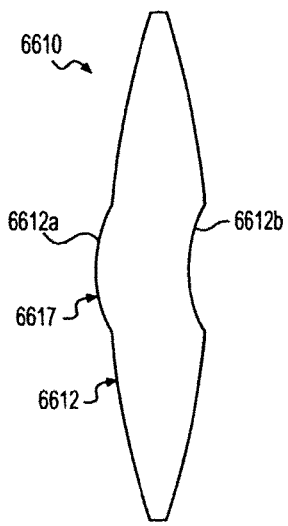

An accommodating intraocular lens 6610 comprising of or consisting of a lens optic 6612 is shown in FIG. 108. The lens optic 6612 comprises a lens optic window 6617 comprising of or consisting of a front positive lens optic surface 6612a and a back negative lens optic surface 6612b.

Figure 109:
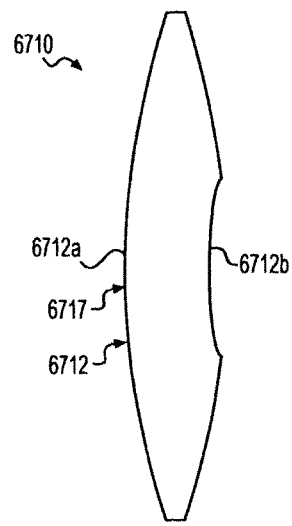

An accommodating intraocular lens 6710 comprising of or consisting of a lens optic 6712 is shown in FIG. 109. The lens optic 6712 comprises a lens optic window 6717 comprising of or consisting of a front positive lens optic surface 6712a (same as or similar to the surface curvature of the front lens surface) and a back negative lens optic surface 6712b.

Figure 110:
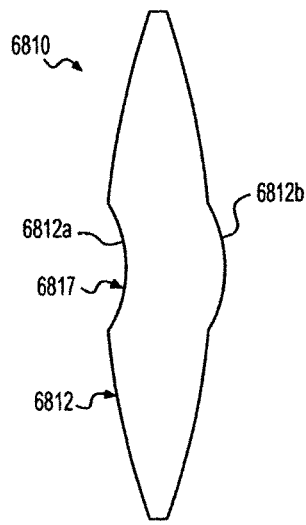

An accommodating intraocular lens 6810 comprising of or consisting of a lens optic 6812 is shown in FIG. 110. The lens optic 6812 comprises a lens optic window 6817 comprising of or consisting of a front negative lens optic surface 6812a and a back positive lens optic surface 6612b.

Figure 111:
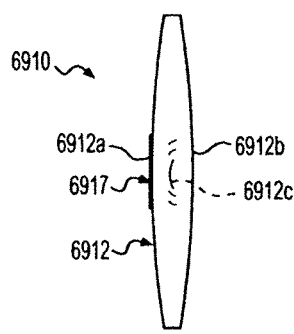

An accommodating intraocular lens 6910 comprising of or consisting of a lens optic 6912 shown in FIG. 111. The lens optic 6912 comprises a lens optic window 6917 comprising of or consisting of a front flat lens optic surface 6812a and a back flat lens optic surface 6812b with a diffractive element 6912c (e.g. diffractive grating).

Figure 112:
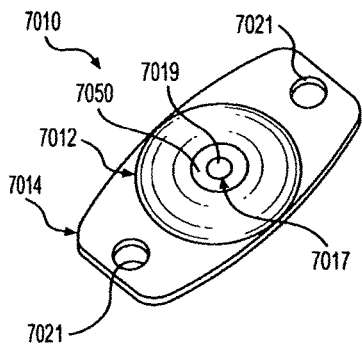
Figure 113:
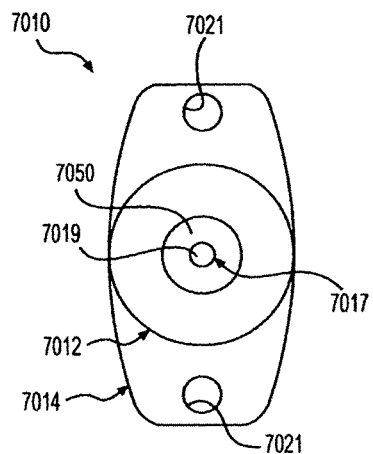
Figure 114:
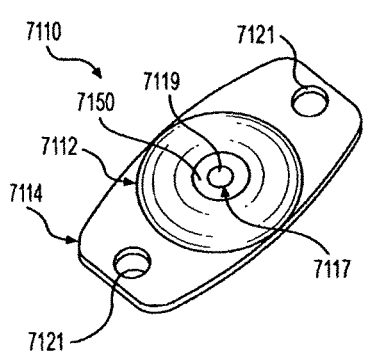
Figure 115:
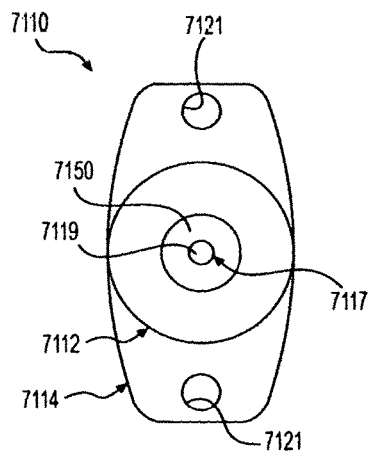

An intraocular lens 7010 comprising or consisting of a lens optic comprising or consisting of a ring-shaped lens optic portion and lens optic window is shown in FIGS. 112 and 113.

The intraocular lens 7010 comprises or consists of a lens optic 7012. The lens optic 7012 comprises or consists of a lens optic window 7017 and a ring-shaped lens optic portion 7019. The lens optic window 7017 is a hole extending through the lens optic 7012.

The ring-shaped lens optic portion 7019 can be configured to effect the optical properties or characteristics of the lens optic 7010. For example, the ring-shaped lens optic portion 7019 can be a ring-shaped zone, ring-shaped mark, a ring-shaped pattern, ring-shaped printed mark on one or both surfaces of the optic portion 7019, a ring-shaped multi-focal lens surface or otherwise a ring-shaped lens portion having optical properties or characteristic different from the surround lens optic portion 7021 and/or the lens aperture 7023.

Further, the ring-shaped lens optic portion 7019 can be a ring-shaped pattern, zone, lens mask, mark, print, and/or insert provided on one or both surfaces of the lens optic, embedded partially into one or both surfaces of the lens optic, and/or fully embedded into the lens optic (e.g. fully embedded inside the lens optic with the lens optic material provided on either side thereof). The ring-shaped lens optic portion 7019 can be provide during making the lens optic and/or added after completion of making the lens optic.

The ring-shaped portion 7019 can be provided by printing, laser, laser treatment on surface, laser treatment inside thickness of lens optic, molding surface, dying, painting, heat application, acid/base treatment, transfer printing, masking, fusion application, spray application, frosting, surface treating, impinging, etching, surfacing, polishing, finishing, or other suitable method. Further, the ring-shaped portion 7019 can be transparent, semi-transparent, frosted, opaque, or combination thereof.

We claim:

1. An accommodating intraocular lens (IOL) configured to be implanted into an eye, the intraocular lens (IOL) comprising:
a lens plate haptic with a central through hole having an inner peripheral edge;
a biconvex lens optic placed within said central through hole and connected to the lens plate haptic, the biconvex lens optic configured to provide static accommodation of vision of the eye, the lens optic having an anterior lens optic surface, a posterior lens optic surface, and an outer peripheral edge, the lens optic comprising a lens optic light window extending at least partially through a thickness of the lens optic, the lens optic light window defined by an anterior flat lens optic surface formed on the anterior lens optic surface of the lens optic, a posterior flat lens optic surface formed on the posterior lens optic surface of the lens optic, and a portion of the lens optic located between the anterior flat lens optic surface and the posterior flat lens optic surface, the anterior flat lens optic surface and the posterior flat lens optic surface being spaced apart a fixed distance and centered on the lens optic, the anterior flat lens optic surface and the posterior flat lens optic surface oriented normal relative to a center optical axis of the lens optic, and
at least two flexible lens arm portions located within said central through hole and extending from the outer peripheral edge of the lens optic to the inner peripheral edge of the central through hole of the plate haptic, each of the at least two flexible lens arm portions being located at a peripheral position of the lens optic, wherein the inner peripheral edge of the central through hole of the plate haptic has a diameter greater than a diameter of the outer peripheral edge of the lens optic, wherein the outer peripheral edge of the lens optic being spaced apart from the inner peripheral edge of the central through hole of the plate haptic, and wherein the lens optic is only connected to the plate haptic at said at least two flexible lens arm portions, wherein the at least two flexible lens arm portions are configured to allow the lens optic to physically axially move relative to the plate haptic along an optical axis of an eye, wherein each of the anterior flat lens optic surface and the posterior flat lens optic surface is circular-shaped, wherein the lens optic light window has a diameter in the range of 0.1 mm to 3.0 mm, wherein the lens optic light window is configured to allow light rays to pass straight through a center thickness of the lens optic with a minimal to none light refraction, and wherein the intraocular lens (IOL) is formed as a one piece structure.

2. The intraocular lens according to claim 1, wherein the two flat lens optic surfaces having the same diameter.

3. The intraocular lens according to claim 1, wherein the light window further comprises a light barrier configured to at least partially isolate light passing through the light window from light passing through a surrounding portion of the lens optic.

4. The intraocular lens according to claim 3, wherein the light barrier is an opaque ring located at a surface the lens optic.

5. The intraocular lens according to claim 4, wherein the opaque ring is located within a thickness of the lens optic.

6. The intraocular lens according to claim 4, wherein the opaque ring is a separate ring structure located within the lens optic.

7. The intraocular lens according to claim 1, wherein the lens optic comprises a light tunnel centered in the anterior flat lens optic surface and posterior flat lens optic surface.

* * * * *